(12) United States Patent
Kumana et al.

(10) Patent No.: US 7,521,071 B2
(45) Date of Patent: Apr. 21, 2009

(54) FORMULATION OF ORAL COMPOSITIONS COMPRISING ARSENIC TRIOXIDE AND METHODS OF USE THEREOF

(75) Inventors: Cyrus Rustam Kumana, Pokfulam (HK); Yok-Lam Kwong, Pokfulam (HK)

(73) Assignee: Versitech Limited (HK)

( * ) Notice: Subject to any disclaimer, the term of this patent is extended or adjusted under 35 U.S.C. 154(b) by 600 days.

(21) Appl. No.: 10/669,869

(22) Filed: Sep. 23, 2003

(65) Prior Publication Data

US 2004/0126434 A1 Jul. 1, 2004

Related U.S. Application Data

(60) Provisional application No. 60/417,200, filed on Oct. 9, 2002, provisional application No. 60/483,014, filed on Jun. 25, 2003.

(51) Int. Cl.
*A61K 33/36* (2006.01)
*A61P 7/00* (2006.01)
*A61P 35/02* (2006.01)

(52) U.S. Cl. .................................................. 424/623
(58) Field of Classification Search .................. 424/623
See application file for complete search history.

(56) References Cited

U.S. PATENT DOCUMENTS

| | | | | |
|---|---|---|---|---|
| 6,723,351 | B2 * | 4/2004 | Warrell et al. | 424/623 |
| 6,875,451 | B2 * | 4/2005 | Ellison et al. | 424/623 |
| 2004/0126434 | A1 * | 7/2004 | Kumana et al. | 424/623 |

FOREIGN PATENT DOCUMENTS

WO  WO 9924029 A1 * 5/1999

OTHER PUBLICATIONS esp@cenet online (http://v3.espacenet.com/textdoc?DB=EPODOC& IDX=CN1370540&QPN=CN1370540), ((CN1370540 (2002)), Abstract.*
Remington's Pharmaceutical Sciences (17th Ed. 1985), pp. 207. 301.*
Au, Wing-Yan et al., "Oral arsenic trioxide in the treatment of relapsed acute promyelocytic leukemia", *Blood* 102(1):407-408 (Jul. 1, 2003).
Au, Wing Y. et al., "Treatment of Relapsed Acute Promyelocytic Leukemia by Arsenic-Based Strategies without Hematopoietic Stem Cell Transplantation in Hong Kong: A Seven-Year Experience", *Blood (ASH Annual Meeting Abstracts)*, 104:Abstract 395 (2004).
Au, Wing-Yan et al., "Successful Treatment of Relapsed Acute Promyelocytic Leukemia in a Patient Receiving Continuous Ambulatory Peritoneal Dialysis With Oral Arsenic Trioxide", *Arch Intern Med.*, 165:1067-1068 (2005).
Au, Wing-Yan et al., "Elemental arsenic entered the cerebrospinal fluid during oral arsenic trioxide treatment of meningeal relapse of acute promyelocytic leukemia", *Blood*, 107(7):3012-3013 (2006).
Kumana, C.R. et al., "Systemic availability of arsenic from oral arsenic-trioxide used to treat patients with hematological malignancies", *Eur J Clin Pharmacol*, 58:521-526 (2002).
Siu, Chung-Wah et al., "Effects of oral arsenic trioxide therapy on QT intervals in patients with acute promyelocytic leukemia: implications on long-term cardiac safety", *Blood*, 0:2006-01-0054 (2006).
Abroun, et al., "Receptor synergy of interleukin-6 (IL-6) and insulin-like growth factor-I in myeloma cells that highly express IL-6 receptor alpha [corrected]", *Blood*, 103(6):2291-8 (2004).
Akay and Gazitt, "Arsenic trioxide selectively induces early and extensive apoptosis via the APO2/caspase-8 pathway engaging the mitochondrial pathway in myeloma cells with mutant p53", *Cell Cycle*, 2(4):358-68 (2003).
Alt, et al., "Phosphorylation-dependent regulation of cyclin D1 nuclear export and cyclin D1-dependent cellular transformation" *Genes Dev*, 14:3102-14 (2000).
Au, et al., "Combined arsenic trioxide and all-trans retinoic acid treatment for acute promyelocytic leukaemia recurring from previous relapses successfully treated using arsenic trioxide", *Br J Haematol.*, 117(1):130-2 (2002).
Bahlis, et al., "Feasibility and correlates of arsenic trioxide combined with ascorbic acid-mediated depletion of intracellular glutathione for the treatment of relapsed/refractory multiple myeloma", *Clin Cancer Res.*, 8(12):3658-68 (2002).
Berenson, et al., "A prospective, open-label safety and efficacy study of combination treatment with melphalan, arsenic trioxide, and ascorbic acid in patients with relapsed or refractory multiple myeloma", *Clin Lymphoma*, 5(2):130-4 (2004).
Burke, et al., "BMS-345541 is a highly selective inhibitor of I kappa B kinase that binds at an allosteric site of the enzyme and blocks NF-kappa B-dependent transcription in mice", *J Biol Chem*, 278:1450-6 (2003).
Camacho, et al., "Leukocytosis and the retinoic acid syndrome in patients with acute promyelocytic leukemia treated with arsenic trioxide", *J. Clin. Oncol.*, 18:2620-5 (2000).
Carpenter, "Employment of the epidermal growth factor receptor in growth factor-independent signaling pathways", *J Cell Biol.*, 146(4):697-702 (1999).
Catley, et al., "Perspectives for combination therapy to overcome drug-resistant multiple myeloma", *Drug Resist Updat.*, 8(4):205-18 (2005).
Chen, et al., "Use of arsenic trioxide (As2O3) in the treatment of acute promyelocytic leukemia (APL): I. As2O3 exerts dose-dependent dual effects on APL cells" *Blood*, 89(9):3345-53 (1997).
Choong and Cohen, "Epidermal growth factor receptor directed therapy in head and neck cancer", *Crit Rev Oncol Hematol.*, 57(1):25-43 (2006).
Cohen, et al., "The expanding role of systemic therapy in head and neck cancer", *J Clin Oncol.*, 22(9):1743-52 (2004).

(Continued)

*Primary Examiner*—Johann R Richter
*Assistant Examiner*—Frank I Choi
(74) *Attorney, Agent, or Firm*—Pabst Patent Group LLP

(57) ABSTRACT

The present invention provides an oral formulation of arsenic trioxide ($As_2O_3$) for the treatment of a variety of hematological malignancies, including acute myeloid leukemia (AML) and acute promyelocytic leukemia (APL). The present invention also provides methods for making the oral arsenic trioxide formulation. Methods of using the oral arsenic trioxide formulation are also described.

14 Claims, 11 Drawing Sheets

OTHER PUBLICATIONS

Figure 1:
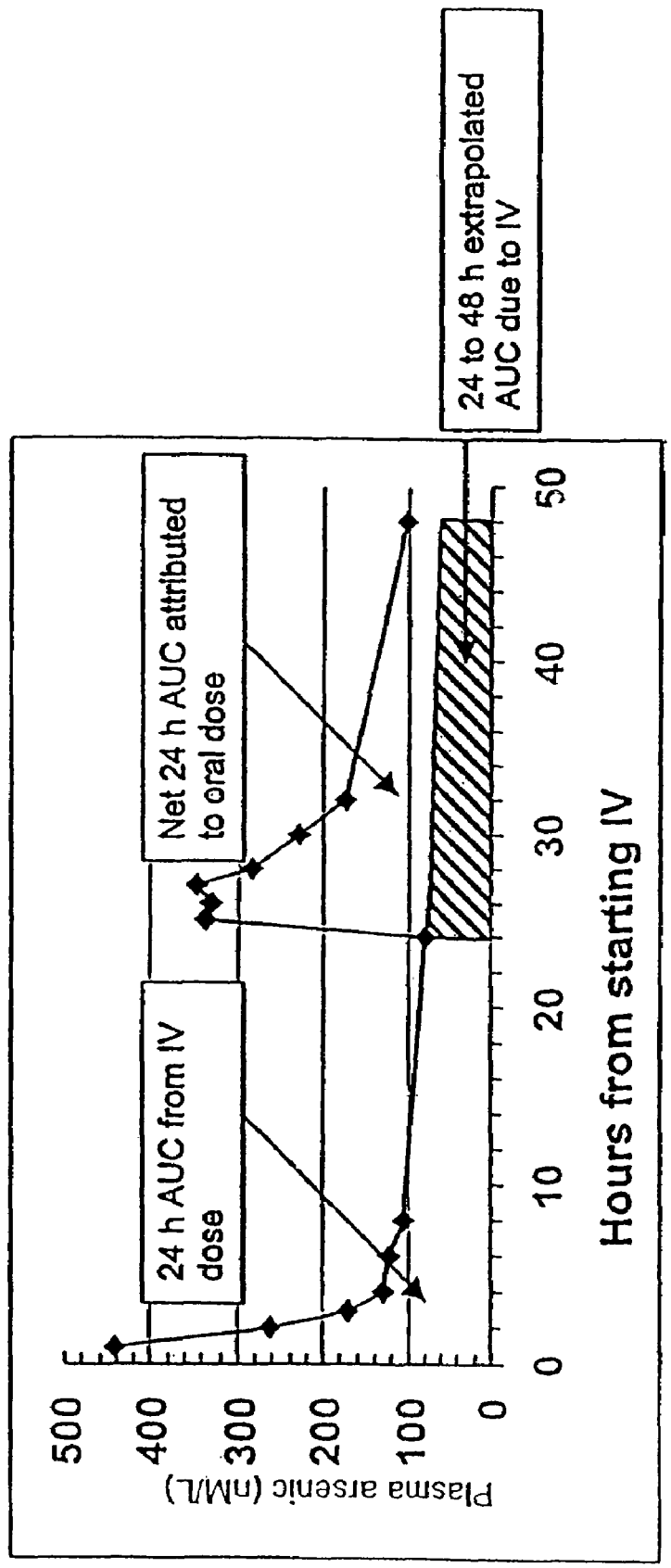
Figure 2A:
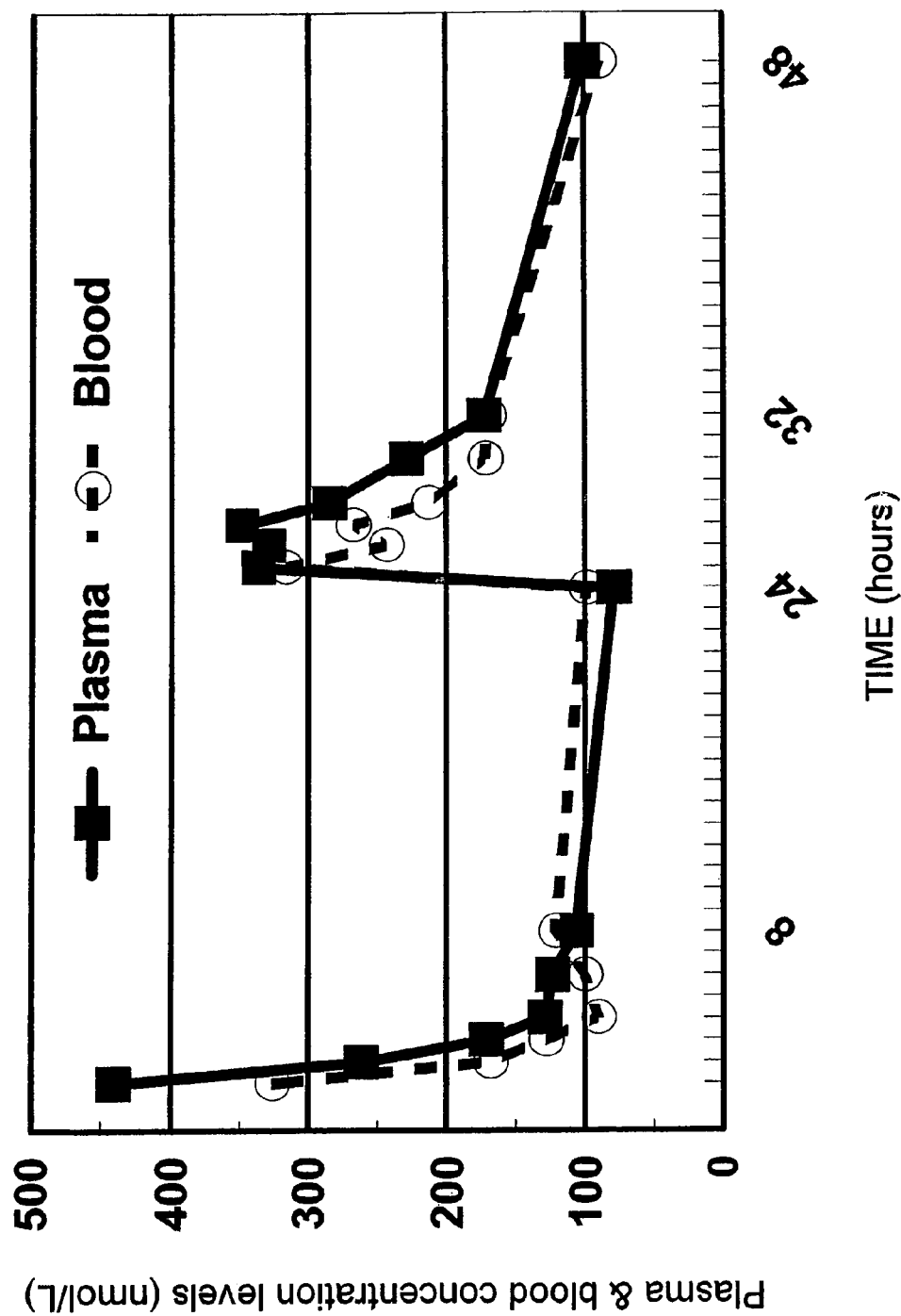
Figure 2F:
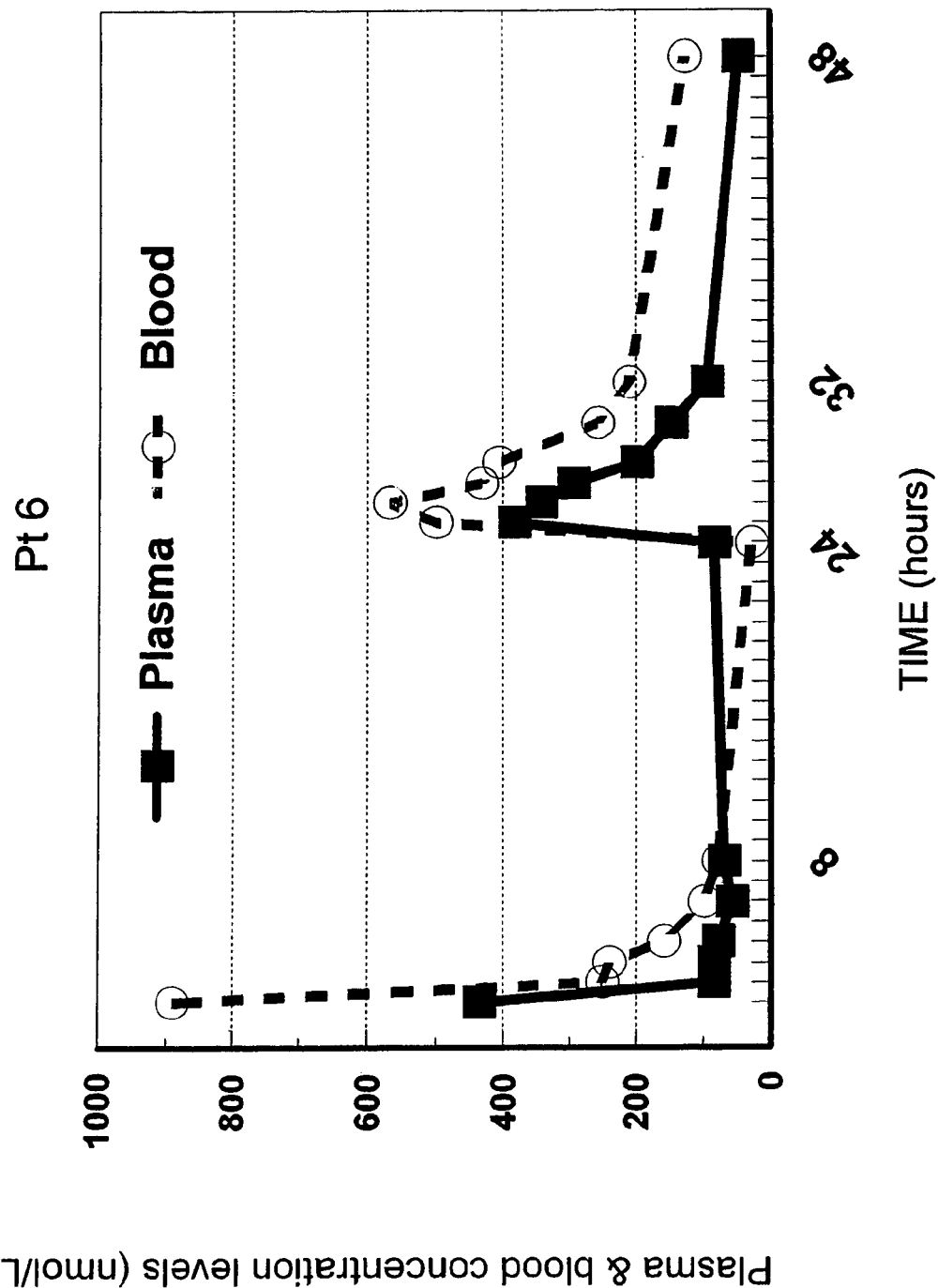
Figure 2G:
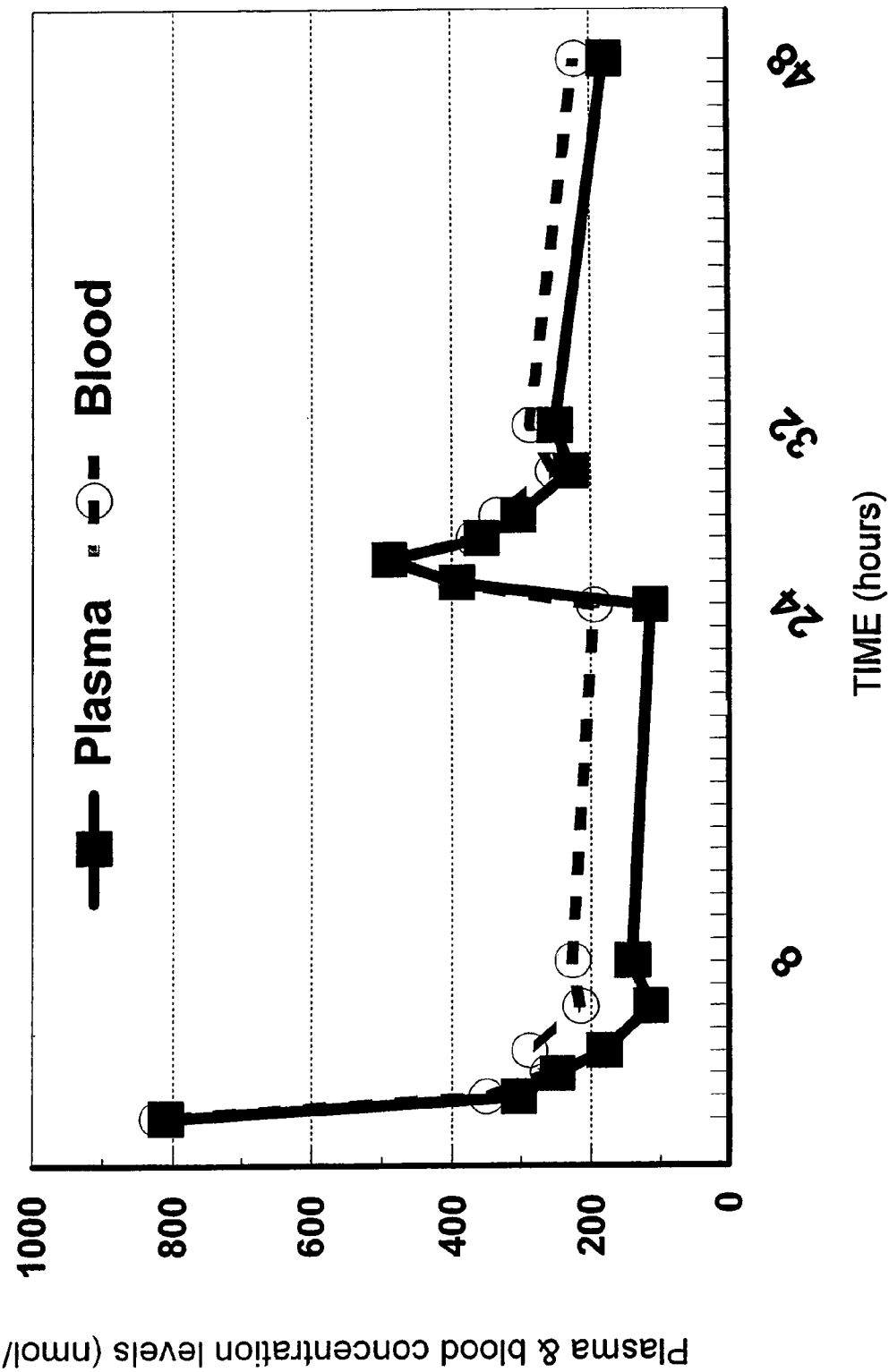
Figure 2H:
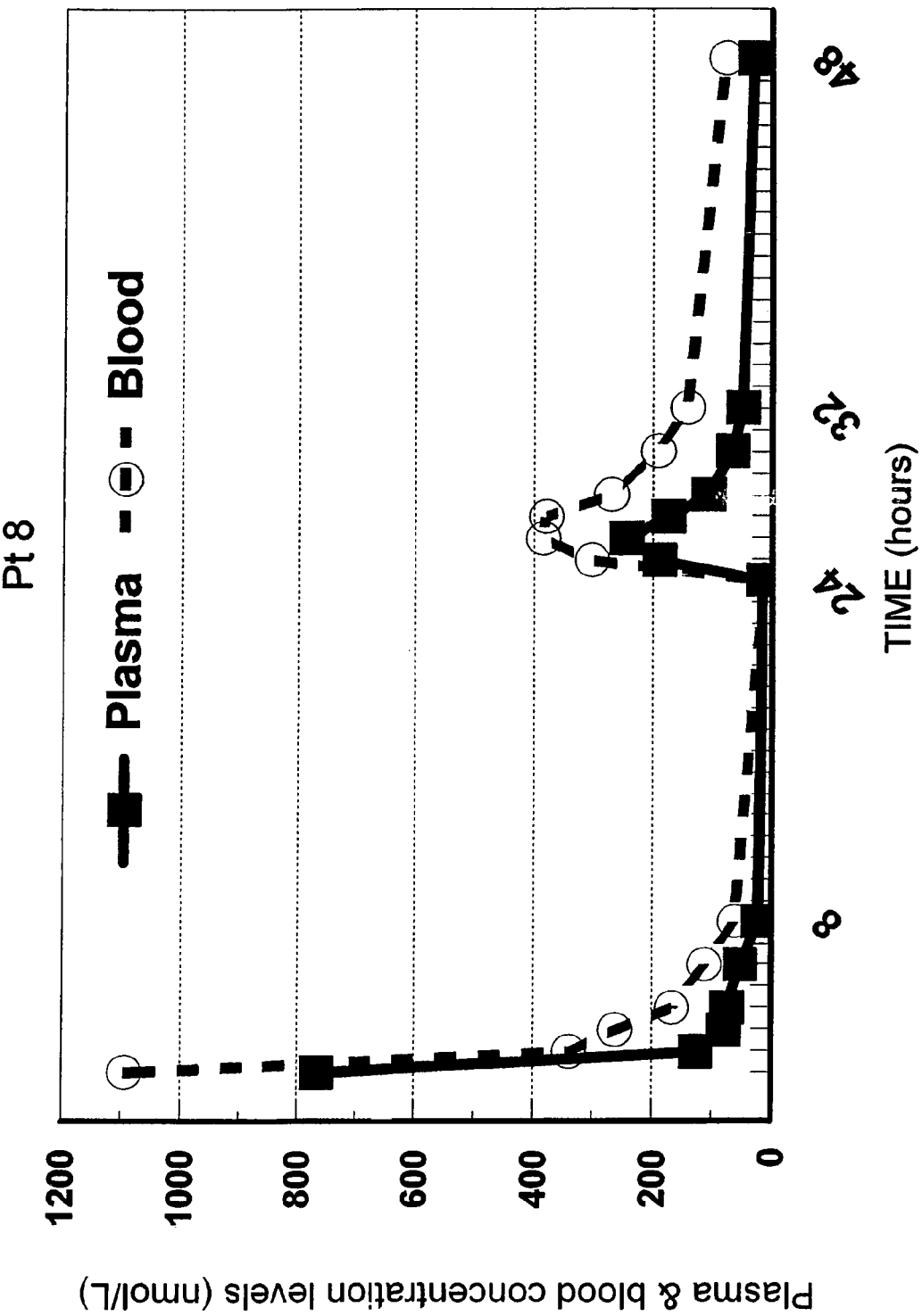
Figure 2I:
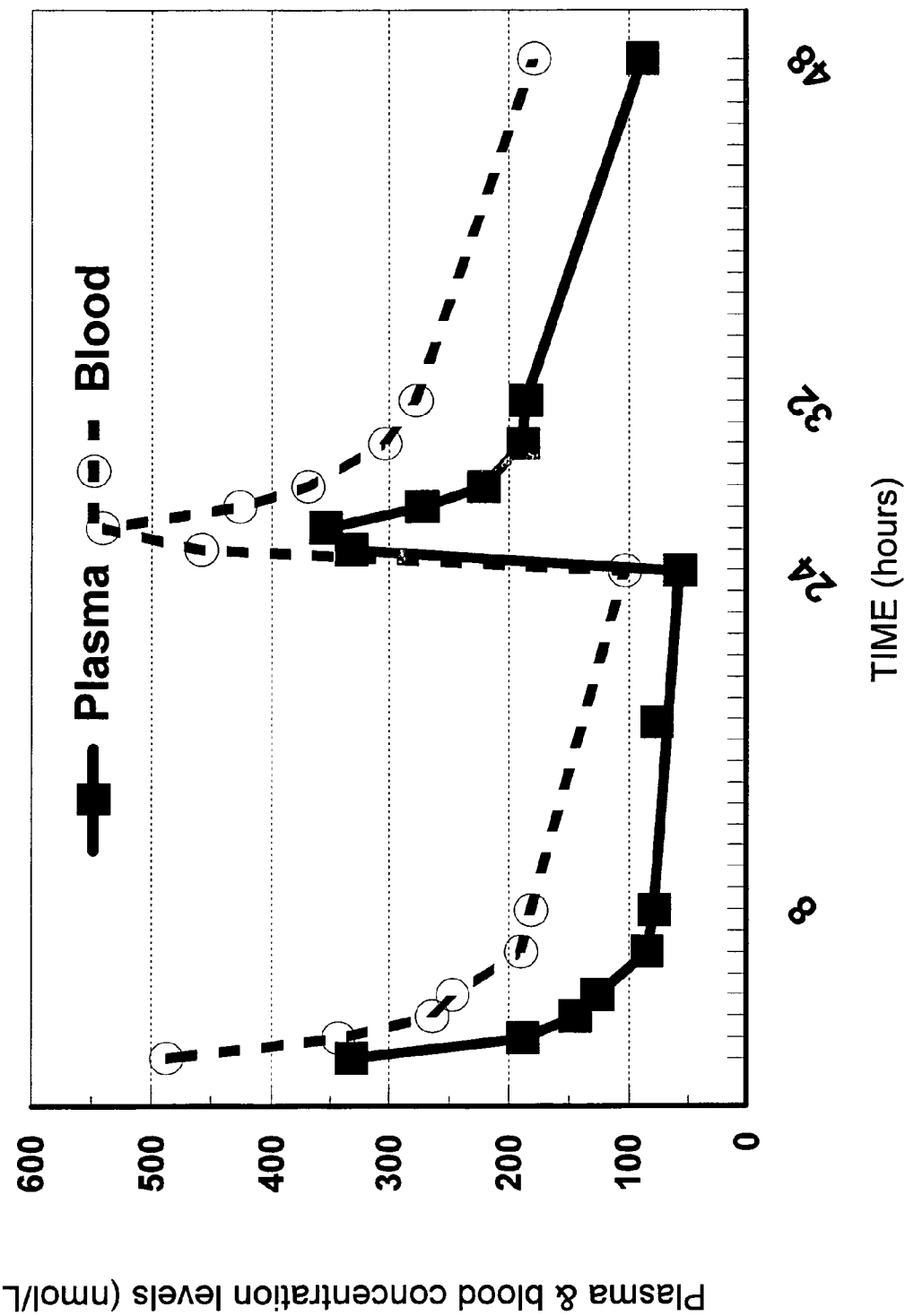

Cole, et al., "Further evidence that the tyrosine phosphorylation of glycogen synthase kinase-3 (GSK3) in mammalian cells is an autophosphorylation event", *Biochem J.*, 377:249-55 (2004).

Cross, et al., "Inhibition of glycogen synthase kinase-3 by insulin mediated by protein kinase B", *Nature*, 378:785-9 (1995).

Davison, et al., "JNK activation is a mediator of arsenic trioxide-induced apoptosis in acute promyelocytic leukemia cells", *Blood*, 103(9):3496-502 (2004).

Del Razo, et al., "Stress proteins induced by arsenic", *Toxicol Appl Pharmacol.*, 177(2):132-48 (2001).

Diehl, et al., "Glycogen synthase kinase-3beta regulates cyclin D1 proteolysis and subcellular localization", *Genes Dev*,12:3499-511 (1998).

Diehl, et al., "Inhibition of cyclin D1 phosphorylation on threonine-286 prevents its rapid degradation via the ubiquitin-proteasome pathway", *Genes Dev*, 11:957-72 (1997).

Fan, et al., "Phospholipase C-independent activation of glycogen synthase kinase-3beta and C-terminal Src kinase by Galphaq", *J Biol Chem*, 278:52432-6 (2003).

Ferlin, et al., "Insulin-like growth factor induces the survival and proliferation of myeloma cells through an interleukin-6-independent transduction pathway", *Br J Haematol.*, 111(2):626-34 (2000).

Forstpointer, et al., "The addition of rituximab to a combination of fludarabine, cyclophosphamide, mitoxantrone (FCM) significantly increases the response rate and prolongs survival as compared with FCM alone in patients with relapsed and refractory follicular and mantle cell lymphomas: results of a prospective randomized study of the German Low-Grade Lymphoma Study Group" *Blood*, 104:3064-71 (2004).

Gartenhaus, et al., "Arsenic trioxide cytotoxicity in steroid and chemotherapy-resistant myeloma cell lines: enhancement of apoptosis by manipulation of cellular redox state", *Clin Cancer Res.*, 8(2):566-72 (2002).

Goy, et al., "Phase II study of proteasome inhibitor bortezomib in relapsed or refractory B-cell non-Hodgkin's lymphoma" *J Clin Oncol*, 23:667-75 (2005).

Grandis, et al., "Levels of TGF-alpha and EGFR protein in head and neck squamous cell carcinoma and patient survival", *J Natl Cancer Inst.*, 90:824-32 (1998).

Guo, et al., "Phosphorylation of cyclin D1 at Thr 286 during S phase leads to its proteasomal degradation and allows efficient DNA synthesis" *Oncogene*, 24:2599-612 (2005).

Guo, et al., "Post-transcriptional regulation of cyclin D1 expression during G2 phase" *Oncogene*, 21:7545-56 2002).

Hartigan, et al., "Glycogen synthase kinase 3beta is tyrosine phosphorylated by PYK2", *Biochem Biophys Res Commun.*, 284:485-9 (2001).

Hartigan, et al., "Transient increases in intracellular calcium result in prolonged site-selective increases in Tau phosphorylation through a glycogen synthase kinase 3beta-dependent pathway", *J Biol Chem*, 274:21395-401 (1999).

Hicke, "Protein regulation by monoubiquitin", *Nat Rev Mol Cell Biol*, 2:195-201 (2001).

Huang, et al., "Acute and chronic arsenic poisoning associated with treatment of acute promyelocytic leukaemia", *Br J. Haematol.*, 103(4):1092-5 (1998).

Hubbard and Till, "Protein tyrosine kinase structure and function", *Annu Rev Biochem.*, 69:373-98 (2000).

Hughes, et al., "Modulation of the glycogen synthase kinase-3 family by tyrosine phosphorylation", *EMBO J*, 12:803-8 (1993).

Hussein, et al., "Phase 2 study of arsenic trioxide in patients with relapsed or refractory multiple myeloma", *Br J Haematol.*, 125(4):470-6 (2004).

Janne, "Ongoing first-line studies of epidermal growth factor receptor tyrosine kinase inhibitors in select patient populations", *Semin Oncol.*, 32(6 Suppl 10):S9-15 (2005).

Jemal, et al., "Cancer statistics, 2005", *CA Cancer J Clin.*, 55(1):10-30 (2005).

Kauffmann-Zeh, et al., "Suppression of c-Myc-induced apoptosis by Ras signalling through PI(3)K and PKB", *Natur*, 385:544-8 (1997).

Kaufmann, et al., "Antitumor activity of rituximab plus thalidomide in patients with relapsed/refractory mantle cell lymphoma", *Blood*, 104:2269-71 (2004).

Kim, et al., "The novel tyrosine kinase ZAK1 activates GSK3 to direct cell fate specification", *Cell*, 99:399-408 (1999).

Kwak, et al., "IkappaB kinase alpha regulates subcellular distribution and turnover of cyclin D1 by phosphorylation", *J Biol Chem*, 280:33945-52 (2005).

Kwong, et al., "Delicious poison: arsenic trioxide for the treatment of leukemia", *Blood*, 89(9):3487-8 (1997).

Kwong, et al., "Arsenic trioxide- and idarubicin-induced remissions in relapsed acute promyelocytic leukaemia: clinicopathological and molecular features of a pilot study", *Am J. Hematol.*, 66:274-9 (2001).

Kwong, "Arsenic trioxide in the treatment of haematological malignancies", *Expert Opin Drug Saf.*, 3(6):589-97 (2004).

Lalemand-Breitenbach, et al., "Role of promyelocytic leukemia (PML) sumolation in nuclear body formation, 11S proteasome recruitment, and As2O3-induced PML or PML/retinoic acid receptor alpha degradation", *J Exp Med.*, 193(12):1361-71 (2001).

Lenz, et al., "Immunochemotherapy with rituximab and cyclophosphamide, doxorubicin, vincristine, and prednisone significantly improves response and time to treatment failure, but not long-term outcome in patients with previously untreated mantle cell lymphoma: results of a prospective randomized trial of the German Low Grade Lymphoma Study Group (GLSG)", *J Clin Oncol.*, 23:1984-92 (2005).

Lesort, et al., "Insulin transiently increases tau phosphorylation: involvement of glycogen synthase kinase-3beta and Fyn tyrosine kinase", *J Neurochem*, 72:576-84 (1999).

Ling, et al., "NF-kappaB-inducing kinase activates IKK-alpha by phosphorylation of Ser-176", *Proc Natl Acad Sci U S A.*, 95:3792-7 (1998).

Liu, et al., "Arsenic trioxide-induced apoptosis in myeloma cells: p53-dependent G1 or G2/M cell cycle arrest, activation of caspase-8 or caspase-9, and synergy with APO2/Trail.", *Blood*, 101(10):4078-87 (2003).

Lu, et al., "Tetra-arsenic tetra-sulfide for the treatment of acute promyelocytic leukemia: a pilot report", *Blood*, 99(9):3136-43 (2002).

Malinin, et al., "MAP3K-related kinase involved in NF-kappaB induction by TNF, CD95 and IL-1", *Nature*, 385:540-4 (1997).

Marmor and Yarden, "Role of protein ubiquitylation in regulating endocytosis of receptor tyrosine kinases", *Oncogene*, 23(11):2057-70 (2004).

Mosesson, et al., "Endocytosis of receptor tyrosine kinases is driven by monoubiquitylation, not polyubiquitylation", *J Biol Chem.*, 278(24):21323-6 (2003).

Munshi, "Arsenic trioxide: an emerging therapy for multiple myeloma", *Oncologist*, 6 Suppl 2:17-21 (2001).

Ni, et al., "Pharmacokinetics of intravenous arsenic trioxide in the treatment of acute promyelocytic leukemia", *Chin Med J (Engl).*, 111(12):1107-10 (1998).

Niu, et al., "Studies on treatment of acute promyelocytic leukemia with arsenic trioxide: remission induction, follow-up, and molecular monitoring in 11 newly diagnosed and 47 relapsed acute promyelocytic leukemia patients", *Blood*, 94(10):3315-24 (1999).

O'Connor, et al., "Phase II clinical experience with the novel proteasome inhibitor bortezomib in patients with indolent non-Hodgkin's lymphoma and mantle cell lymphoma", *J Clin Oncol*, 23:676-84 (2005).

Ohnishi, et al., "Prolongation of the QT interval and ventricular tachycardia in patients treated with arsenic trioxide for acute promyelocytic leukemia", *Ann Intern Med.*, 133(11):881-5 (2000).

Park, et al., "Arsenic trioxide-mediated growth inhibition in MC/CAR myeloma cells via cell cycle arrest in association with induction of cyclin-dependent kinase inhibitor, p21, and apoptosis", *Cancer Res.*, 60(11):3065-71 (2000).

Pomerantz and Grandis, "The epidermal growth factor receptor signaling network in head and neck carcinogenesis and implications for targeted therapy", *Semin Oncol.*, 31(6):734-43 (2004).

Qian, et al., "New perspectives in arsenic-induced cell signal transduction", *J Inorg Biochem.*, 96(2-3):271-8 (2003).

Qiang, et al., "Insulinlike growth factor-I signaling in multiple myeloma: downstream elements, functional correlates, and pathway cross-talk", *Blood*, 99(11):4138-46 (2002).

Romaquera, et al., "High rate of durable remissions after treatment of newly diagnosed aggressive mantle-cell lymphoma with rituximab plus hyper-CVAD alternating with rituximab plus high-dose methotrexate and cytarabine" *J Clin Oncol*, 23:7013-23 (2005).

Roodman, "Pathogenesis of myeloma bone disease", *Blood Cells Mol Dis.*, 32(2):290-2 (2004).

Sayas, et al., "GSK-3 is activated by the tyrosine kinase Pyk2 during LPA1-mediated neurite retraction", *Mol Biol Cell*, 17:1834-44 (2006).

Shen, et al., "Use of arsenic trioxide (As2O3) in the treatment of acute promyelocytic leukemia (APL): II. Clinical efficacy and pharmacokinetics in relapsed patients", *Blood*, 89(9):3354-60 (1997).

Sherr, "Cancer cell cycles" *Science*, 274:1672-7 (1996).

Sherr, et al., "The RB and p53 pathways in cancer" *Cancer Cell*, 2:103-112 (2002).

Simeonova, et al., "c-Src-dependent activation of the epidermal growth factor receptor and mitogen-activated protein kinase pathway by arsenic. Role in carcinogenesis", *J Biol Chem.*, 277(4):2945-50 (2002).

Soignet, et al., "Complete remission after treatment of acute promyelocytic leukemia with arsenic trioxide", *N Engl J Med.*, 339(19):1341-8 (1998).

Soignet, et al., "United States multicenter study of arsenic trioxide in relapsed acute promyelocytic leukemia", *J Clin Oncol.*, 19(18):3852-60 (2001).

Sternsdorf, et al., PIC-1/SUMO-1-modified PML-retinoic acid receptor alpha mediates arsenic trioxide-induced apoptosis in acute promyelocytic leukemia , *Mol Cell Biol.*, 19(7):5170-8 (1999).

Swerdlow, et al., Mantle Cell Lymphoma, in Jaffe, E.S. et al. Ied.), WHO Classification of Tumors, (2001) 168-170.

Tai, et al., "Insulin-like growth factor-1 induces adhesion and migration in human multiple myeloma cells via activation of beta 1-integrin and phosphatidylinositol 3'-kinase/AKT signaling", *Cancer Res.*, 63(18):5850-8 (2003).

Tallman, et al., "Acute promyelocytic leukemia: evolving therapeutic strategies", *Blood*, 99(3):759-67 (2002).

The Non-Hodgkin's Lymphoma Classification Project. A clinical evaluation of the International Lymphoma Study Group classification of non-Hodgkin's lymphoma, *Blood*, 89:3909-3918 (1997).

Tsujimoto, et al., "Clustering of breakpoints on chromosome 11 in human B-cell neoplasms with the t(11;14) chromosome translocation", *Nature*, 315:340-3 (1985).

Tsujimoto, et al., "Molecular cloning of the chromosomal breakpoint of B-cell lymphomas and leukemias with the t(11;14) chromosome translocation" *Science*, 224:1403-6 (1994).

Van De Donk, et al., "Growth factors and antiapoptotic signaling pathways in multiple myeloma", *Leukemia*, 19(12):2177-85 (2005).

Vanhaesebroeck, et al., "Phosphoinositide 3-kinases: a conserved family of signal transducers", *Trends Biochem Sci*, 22:267-72 (1997).

Witzig "Current treatment approaches for mantle-cell lymphoma", *J Clin Oncol*, 23:6409-14 (2005).

Witzig, et al., "Phase II trial of single-agent temsirolimus (CCI-779) for relapsed mantle cell lymphoma", *J Clin Oncol*, 23:5347-56 (2005).

Yamauchi, et al., "Metabolism and excretion of orally administered arsenic trioxide in the hamster", *Toxicology*, 34(2):113-21 (1985).

Yang and Frenkel, "Arsenic-mediated cellular signal transduction, transcription factor activation, and aberrant gene expression: implications in carcinogenesis", *Environ Pathol Toxicol Oncol.*, 21(4):331-42 (2002).

* cited by examiner

Pt 1

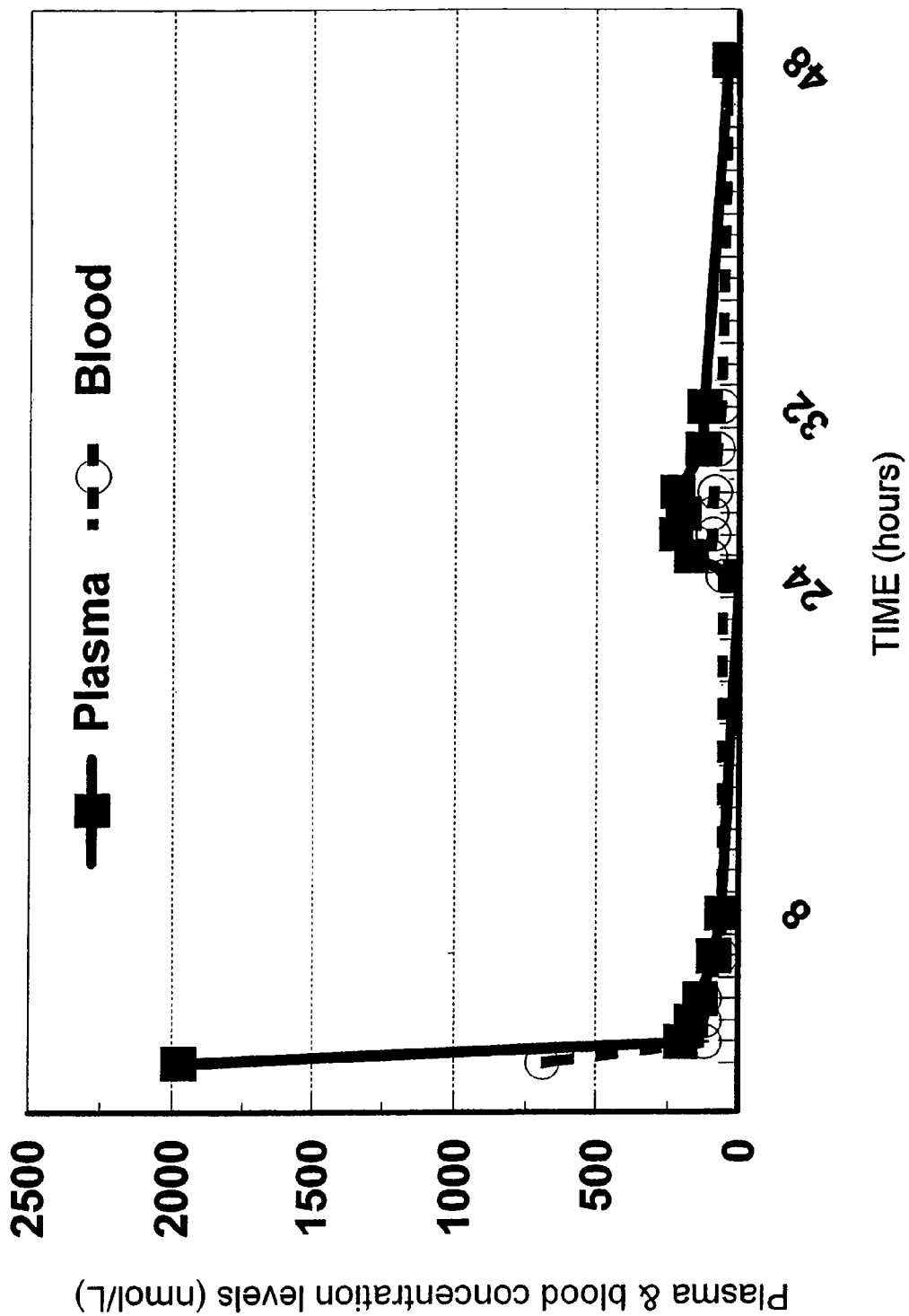

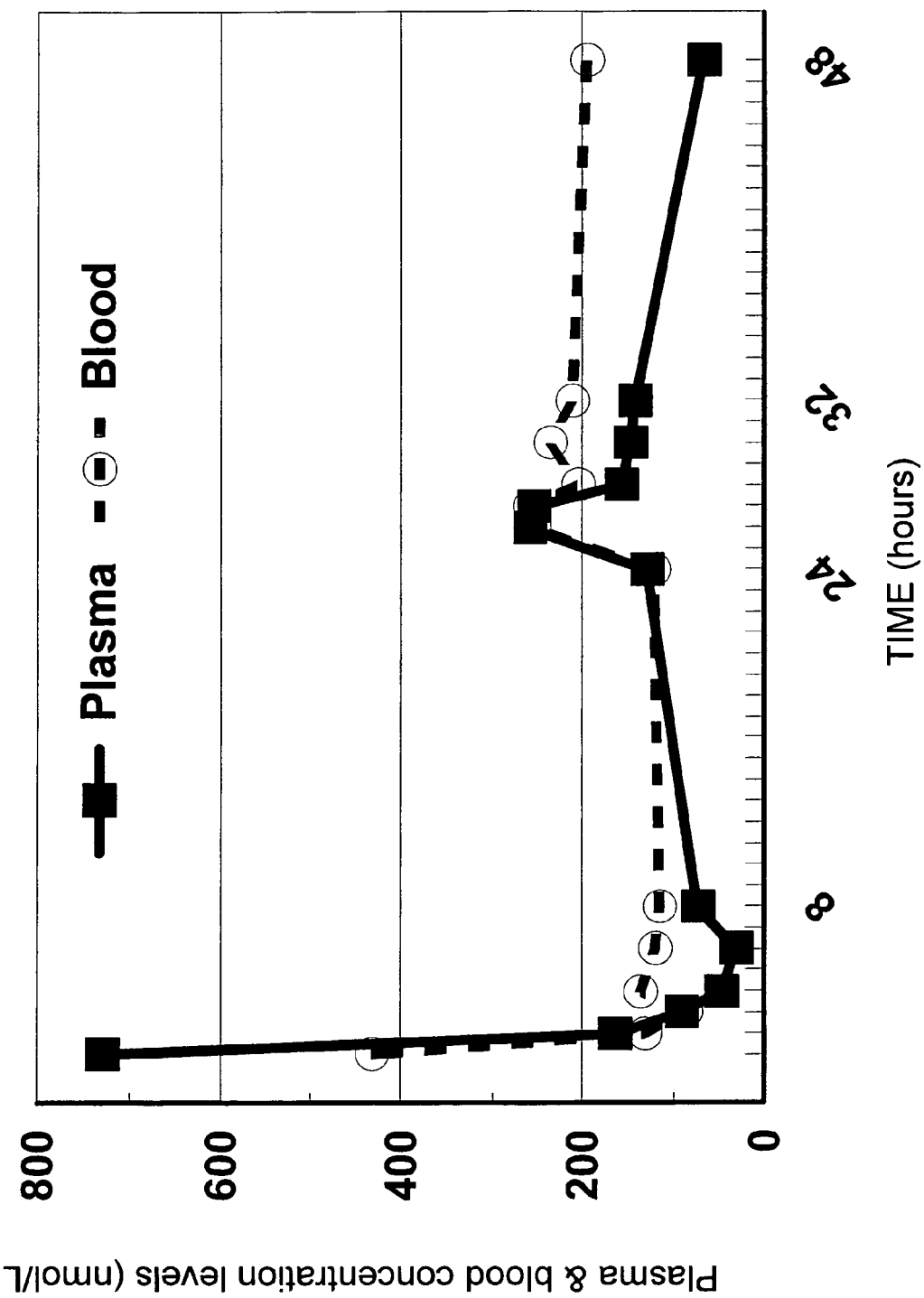

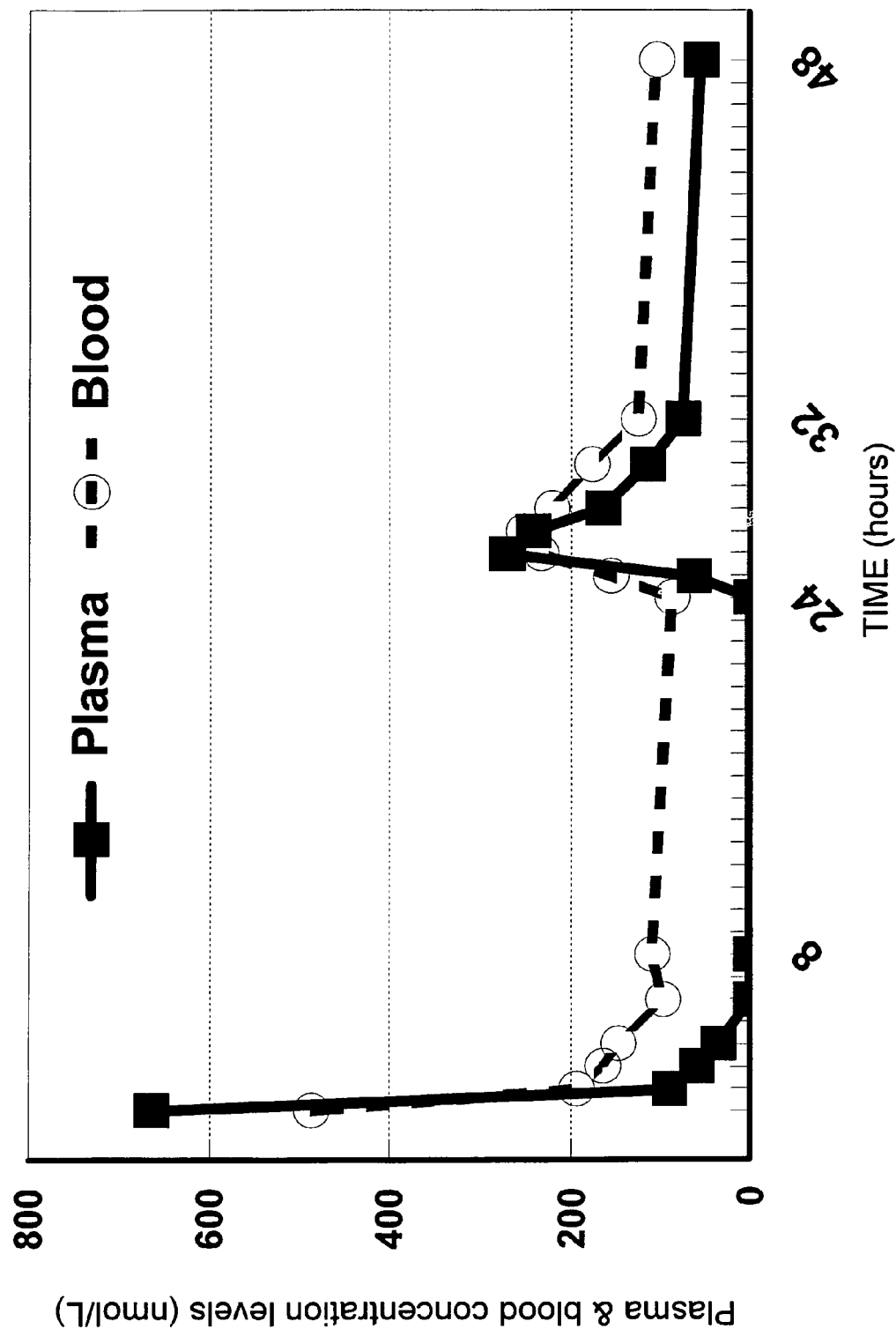

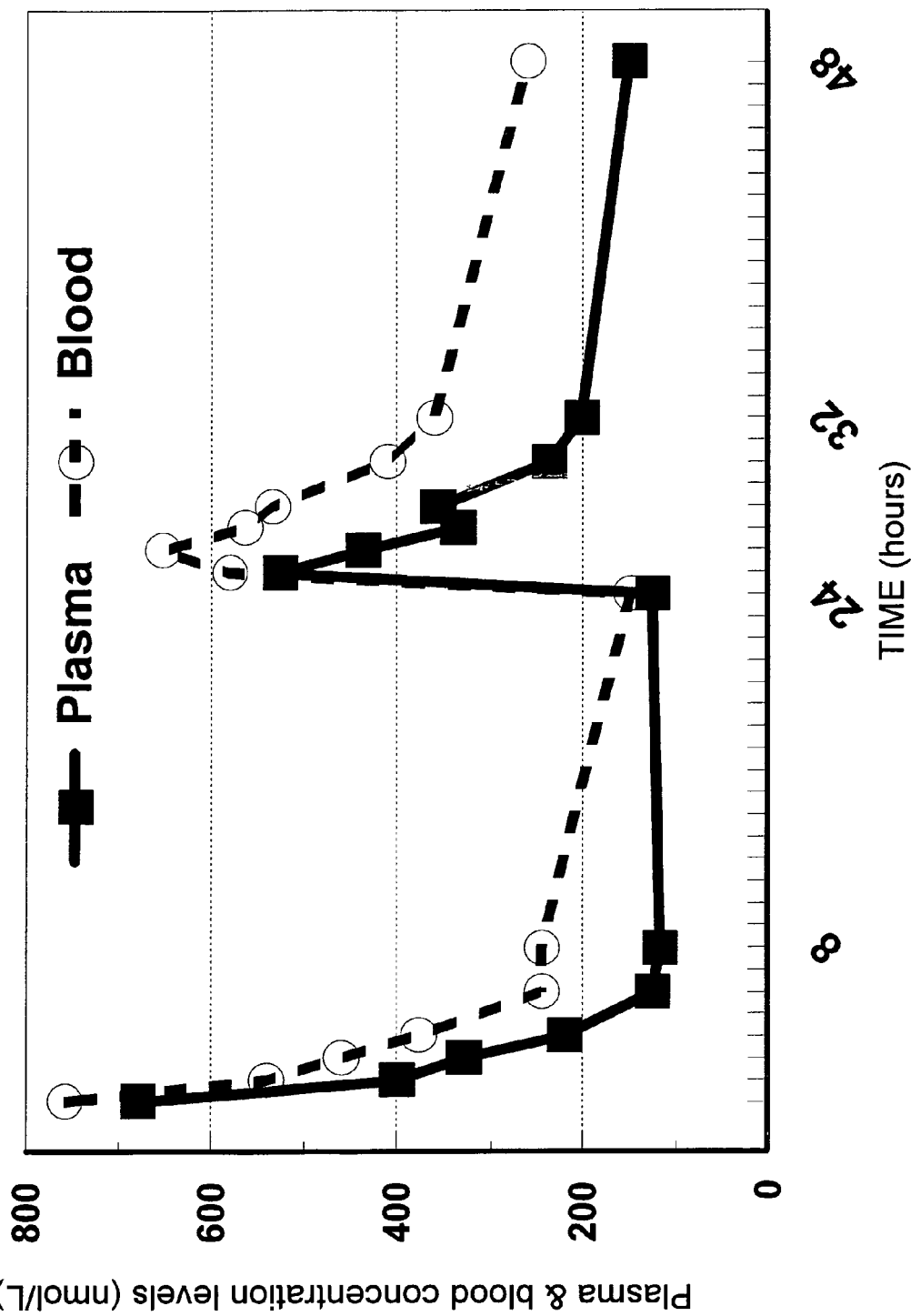

Pt 8

Pt 9

Fig. 3

Clinicopathologic features and outcome of 12 consecutive patients with relapsed acute promyelocytic leukemia treated with oral $As_2O_3$

| sex/age | status | previous induction treatment | Time from last CR | relapse Hb | WBC | Plat | Oral $As_2O_3$ therapy duration | additional Rx | result | Consolidation | Latest PCR¹ | DFS | Remarks |
|---|---|---|---|---|---|---|---|---|---|---|---|---|---|
| 1* M/23 | R1 | ATRA + Dauno | 11 m | 15.6 | 2.1 | 87 | 59 d | Ida | CR | Ida | +(dead) | 13 m | |
| 2* M/33 | R2 | i.v. $As_2O_3$ | 10 m | 14.0 | 2.5 | 25 | 76 d | ATRA | NR | . | . | . | . |
| 3* F/13 | R2 | Dauno / i.v. $As_2O_3$ + Ida | 25 m | 13.4 | 2.1 | 20 | 32 d | ATRA | CR | $As_2O_3$ + ATRA | -(18 m) | 19 m+ | . |
| 4 M/54 | R1 | ATRA + i.v. $As_2O_3$ | 12 m | 8.6 | 1.2 | 15 | 30 d | ATRA | CR | $As_2O_3$ + ATRA | -(18 m) | 19 m+ | . |
| 5* M/32 | R1 | ATRA + Dauno | 100 m | 8.3 | 34.8 | 81 | 40 d | Ida | CR | Ida | -(18 m) | 18 m+ | mother: AML |
| 6 F/32 | R2 | ATRA + Dauno + MP | 22 m | 14.5 | 2.4 | 177 | 33 d | . | CR | Ida | -(18 m) | 18 m+ | . |
| 7* F/45 | R2 | ATRA + Dauno / i.v. $As_2O_3$ + Ida | 12 m | 12.2 | 0.8 | 84 | 51 d | . | CR | Ida | -(12 m) | 18 m+ | . |
| | | | 17 m | 11.2 | 1.9 | 50 | 37 d | ATRA | CR | $As_2O_3$ + ATRA | -(14 m) | 17 m+ | . |
| 8 F/65 | R1 | ATRA | 16 m | 7.2 | 2.8 | 141 | 28 d | . | CR | $As_2O_3$ + ATRA | -(12 m) | 15 m+ | CRF due to DM on CAPD, Ida consolidation omitted due to CRF |
| 9 F/18 | R2 | ATRA + Dauno / i.v. $As_2O_3$ + Ida | 12 m | 10.1 | 1.9 | 180 | 28 d | ATRA | CR | $As_2O_3$ + ATRA | -(12 m) | 14 m+ | . |
| 10* F/18 | R1 | ATRA + Dauno | 12 m | 8.2 | 12.6 | 54 | 44 d | Ida | CR | Ida | -(6 m) | 9 m+ | . |
| 11* M/45 | R1 | ATRA + Dauno | 240 m | 4.2 | 0.6 | 9 | 22 d | . | CR | $As_2O_3$ | -(3 m) | 7 m+ | Ida consolidation omitted due to high cumulative doses of anthracycline |
| 12 F/40 | R1 | ATRA + Ara-c | 23 m | 8.5 | 6.5 | 39 | 28 d | Ida | CR | Ida | -(3 m) | 6 m+ | CRHD, double valve rep |

*: pharmacokinetic data of oral $As_2O_3$ have previously been reported⁶
1: PCR for *PML/RARA*, +: positive, -: negative, (time from initial diagnosis)
M: male; F: female, CR: complete remission; NR: non-remission; R1: first relapse; R2: second relapse
CBC: complete blood count; Hb: hemoglobin (g/dL); WBC: white blood cell count (x 10⁹/L); Plat: platelet count (x 10⁹/L)
m: months; d: days; DFS: disease free survival
ATRA: all-trans retinoic acid; Dauno: daunorubicin; Ida: idarubicin; Ara-c: cytosine arabinoside
CA: carcinoma; AML: acute myeloid leukemia; CRF: chronic renal failure; DM: diabetes mellitus
CAPD: continuous ambulatory peritoneal dialysis; CRHD: chronic rheumatic heart disease; rep: replacement

FORMULATION OF ORAL COMPOSITIONS COMPRISING ARSENIC TRIOXIDE AND METHODS OF USE THEREOF This application claims priority benefit to U.S. provisional application No. 60/417,200, filed Oct. 9, 2002; and U.S. provisional application No. 60/483,014, filed Jun. 25, 2003, each of which is incorporated herein by reference in its entirety.

1. INTRODUCTION

The present invention relates to an oral formulation of arsenic trioxide ($As_2O_3$) for the treatment of various hematological malignancies, including acute myeloid leukemia (AML) and acute promyelocytic leukemia (APL). The formulation provides the systemic bioavailability comparable to that of intravenous (IV) administration of arsenic trioxide currently practiced. The oral formulation of the present invention exhibits the shelf life of more than three (3) months and provides a much more convenient, less risky and less expensive method of administering arsenic trioxide than the intravenous administration methods. The present invention also relates to a method for preparing the oral formulation of the present invention and a method for treating a subject with hematological malignancies using the oral formulation.

2. BACKGROUND OF THE INVENTION

2.1 Hematological Malignancies

Hematological malignancies are cancers of the body's blood-forming and immune systems. Hematological malignancies include leukemia, lymphoma (both Hodgkin's disease and non-Hodgkin's lymphoma), and myeloma. The abnormal cell growth interferes with the body's production of healthy blood cells, thus making the body unable to protect itself against infections.

New cases of hematological malignancies account for 9 percent of cancer cases diagnosed in the United States, and about 59,200 persons are killed by the diseases each year. Many of these disease occur in children.

2.1.1 Leukemia

Leukemia is a cancer of the bone marrow and blood. It is characterized by the uncontrolled growth of blood cells. About 30,000 new cases of leukemia in the United States are reported each year. Most cases occur in older adults, though leukemia is the most common type of childhood cancer.

Leukemia is either acute or chronic. In acute leukemia, the abnormal blood cells are blasts that remain very immature and cannot carry out their normal functions. The number of blasts increases rapidly, and the disease gets worse quickly. In chronic leukemia, some blast cells are present, but in general, these cells are more mature and can carry out some of their normal functions. Also, the number of blasts increases less rapidly than in acute leukemia. As a result, chronic leukemia gets worse gradually.

Leukemia can arise in either of the two main types of white blood cells—lymphoid cells (lymphocytic leukemia) or myeloid cells (myeloid or myelogenous leukemia). Common types of leukemia include acute lymphocytic leukemia (ALL); acute myeloid leukemia (AML) (sometimes called acute nonlymphocytic leukemia (ANLL)) such as myeloblastic, promyelocytic, myelomonocytic, monocytic, erythroleukemia leukemias and myelodysplastic syndrome; chronic lymphocytic leukemia (CLL); chronic myeloid (granulocytic) leukemia (CML); chronic myelomonocytic leukemia (CMML); hairy cell leukemia; and polycythemia vera.

2.1.2 Lymphoma

There are two main types of lymphoma—Hodgkin's disease and non-Hodgkin's lymphoma. Hodgkin's disease, also known as Hodgkin's lymphoma, is a special form of lymphoma in which there is a particular cell known as the Reed Sternberg (R-S) cell. This cell is not usually found in other lymphomas.

The cause for Hodgkin's disease is unknown. Hodgkin's disease, like other cancers, is not infectious and cannot be passed onto other people. It is not inherited. The first symptom of Hodgkin's disease is usually a painless swelling in the neck, armpits or groin. Other symptoms may include night sweats or unexplained fever, weight loss and tiredness, cough or breathlessness, and persistent itch all over the body.

There are about 20 different types of non-Hodgkin's lymphoma. Non-Hodgkin's lymphomas are categorized according to their appearance under the microscope and the cell type (B-cell or T-cell). Risk factors include old age, female, weakened immune system, human T-lymphotropic virus type 1 (HTLV-1) and Epstein-Barr virus infection, and exposure to chemicals such as pesticides, solvents, and fertilizers.

2.1.3 Myeloma

Myeloma is a malignant tumor composed of plasma cells of the type normally found in the bone marrow. Myeloma cells tend to collect in the bone marrow and in the hard, outer part of bones. Sometimes they collect in only one bone and form a single mass, or tumor, called a plasmacytoma. In most cases, however, the myeloma cells collect in many bones, often forming many tumors and causing other problems. When this happens, the disease is called multiple myeloma such as but not limited to giant cell myeloma, indolent myeloma, localized myeloma, multiple myeloma, plasma cell myeloma, sclerosing myeloma, solitary myeloma, smoldering multiple myeloma, nonsecretary myeloma, osteosclerotic myeloma, plasma cell leukemia, solitary plasmacytoma, and extramedullary plasmacytoma.

Myelodysplastic syndromes are disorders in which the bone marrow produces ineffective and abnormal looking cells on one or more types (white blood cells, red blood cells or platelets). The majority of patients are men over sixty. Secondary myelodysplastic syndromes are seen following the use of chemotherapy and irradiation.

Signs and symptoms depend on the types of cells that are affected. Abnormal white cells make people more susceptible to infections; abnormal platelets make people more susceptible to bruising and spontaneous hemorrhages; and abnormal red blood cells causes anemia and fatigue.

While chemotherapy and radiation are useful in the treatment of hematological malignancies, there is a continued need to find better treatment modalities and approaches to manage the disease that are more effective and less toxic, especially when clinical oncologists are giving increased attention to the quality of life of cancer patients. The present invention provides an alternative approach to hematological malignancies therapy and management of the disease by using an oral composition comprising arsenic trioxide.

2.2 Arsenic

Arsenic has been used medicinally for over 2,000 years. In the 18th century, a solution of arsenic trioxide (empirical formula $As_2O_3$) in 1% w/v potassium bicarbonate (Fowler's solution) was developed to treat a variety of infectious and malignant diseases. Its efficacy in suppressing white cells was first described in 1878 (Kwong Y. L. et al. Delicious poison: arsenic trioxide for the treatment of leukemia, *Blood* 1997; 89:3487-8). Arsenic trioxide was therefore used to treat chronic myelogenous leukemia, until more potent cytotoxic drugs superseded it in the 1940s. However, there was a resurgence of interest in such therapy, when arsenic trioxide was found to induce apoptosis and differentiation in acute promyelocytic leukemia (APL) cells (Chen G. Q. et al. Use of arsenic trioxide ($As_2O_3$) in the treatment of acute promyelocytic leukemia (APL): I. $As_2O_3$ exerts dose-dependent dual effect on APL cells in vitro and in vivo, *Blood* 1997;89:3345-53; Soignet S. L. et al. United States multicenter study of arsenic trioxide in relapsed acute promyelocytic leukemia. *J Clin Oncol.* 2001;19:3852-60). The clinical implications of these in vitro observations have since been verified, as arsenic trioxide induces remissions in over 90% of such patients (Shen Z. X. et al. Use of arsenic trioxide ($As_2O_3$) in the treatment of acute promyelocytic leukemia (APL): II. Clinical efficacy and pharmacokinetics in relapsed patients, *Blood* 1997;89:3354-60; Soignet S. L. et al. Complete remission after treatment of acute promyelocytic leukemia with arsenic trioxide, *N Engl J Med* 1998;339:1341-8; Niu C. et al., Studies on treatment of acute promyelocytic leukemia with arsenic trioxide: remission induction, follow-up and molecular monitoring in 11 newly diagnosed and 47 relapsed acute promyelocytic leukemia patients, *Blood* 1999;94:3315-24).

A typical course of arsenic trioxide involves daily intravenous (IV) administration for 4 to 8 weeks and the attendant inconvenience, risks and expense of maintaining suitable vascular access and prolonged hospitalization. Currently, there is no oral arsenic trioxide for clinical use. Fowler's solution is no longer detailed in modem pharmacopoeias or listed in formularies (1941, Arsenum. Martindale, *The Extra Pharmacopoeia* 22:209-15; British Pharmacopoeia. London: Her Majesty's Stationery Office, 1988; Appendix 1A, p A12). Formulation of arsenic trioxide for oral administration could therefore offer distinct advantages. The inventors have recently developed an oral preparation of arsenic trioxide useful for achieving total blood cell and plasma levels of elemental arsenic comparable with those of intravenous arsenic trioxide (Kumana C. R. et al. Systemic availability of oral arsenic-trioxide used for treatment of patients with haematological malignancies. *Eur J Clin Pharmacol.* 2002;58:521-526, which is incorporated by reference herein in its entirety).

3. SUMMARY OF THE INVENTION

The present invention provides an oral preparation of arsenic trioxide ($As_2O_3$) for the treatment of patients with hematological malignancies, in particular, relapsed acute myeloid leukemia (AML) such as myeloblastic, promyelocytic, myelomonocytic, monocytic, erythroleukemia leukemias and myelodysplastic syndrome, and relapsed acute promyelocytic leukemia (APL). A primary objective was to test whether the systemic bioavailability of the oral formulation was comparable to intravenous administration. A secondary objective was to delineate the extent of $As_2O_3$ accumulation in the cellular components of blood and by inference bone marrow cells (the presumed site of action).

In certain embodiments, the invention relates to an oral composition comprising arsenic trioxide useful for treating hematological malignancies. In one embodiment, the oral arsenic trioxide composition is prepared by the steps of: (1) adding arsenic trioxide to sterile water to form a first solution; (2) adding sodium hydroxide to the first solution to form a second solution; (3) adding sterile water to the second solution to form a third solution; (4) adding hydrochloric acid to the third solution to form a fourth solution; and (5) adding diluted hydrochloric acid and sterile water to the fourth solution to form a final solution. In a specific embodiment, the arsenic trioxide is a powder that has at least 90%, 95%, 96%, 97%, 98% or 99% purity. Preferably, the arsenic trioxide powder is completely dissolved prior to adding the hydrochloric acid. In another specific embodiment, the pH of the final arsenic trioxide solution is about 6.0, 6.5, 7.0, 7.5, or 8.0, preferably about 7.2. In another specific embodiment, the final solution has an arsenic trioxide concentration of 1 mg/ml.

The invention also relates to methods of making the oral arsenic trioxide composition. In a preferred embodiment, the method for making the arsenic trioxide composition comprises the steps of: (1) adding 500 mg of arsenic trioxide to 150 ml of sterile water to form a first solution; (2) adding 3M sodium hydroxide to the first solution to form a second solution; (3) adding 250 ml of sterile water to the second solution to form a third solution; (4) adding 6M hydrochloric acid to the third solution to form a fourth solution; and (5) adding dilute hydrochloric acid and sterile water to the fourth solution to form a final solution.

The invention further relates to methods of using the oral arsenic trioxide composition to treat hematological malignancies in a subject. The subject is selected from the group consisting of a cow, a pig, a horse, a sheep, a dog, a cat, a chicken, a duck, a monkey, a rat, a mouse, and a human. Preferably, the subject is a mammal, more preferably a primate, and most preferably a human.

In preferred embodiments, the arsenic trioxide composition is orally administered to a subject with hematological malignancies. The arsenic trioxide composition can be administered to the subject prior to, during, or after conventional treatments for hematological malignancies (e.g., chemotherapy, radiation).

4. BRIEF DESCRIPTION OF THE DRAWINGS

FIG. 1 shows a representative estimation of arsenic level versus time curve (AUC) attributed to intravenous and oral dosing with arsenic trioxide in a single patient. All AUCs were computed using the trapezoid rule. The net 24 h AUC attributable to oral dosing was calculated as the difference between the gross 24-48 h AUC on day 2 and the corresponding AUC attributable to intravenous dosing. The latter AUC was calculated using the extrapolated arsenic level derived from estimates of that patient's elimination pharmacokinetics on day 1 (see Table IV). FIG. 1 is adopted from Kumana et al., *Eur J Clin Pharmacol.* (2002) 58:521-6, which is incorporated herein by reference in its entirety.

FIGS. 2*a*-2*i* show the arsenic concentrations of all nine (9) patients in plasma and whole blood arsenic concentrations on day 1 and day 2. FIGS. 2*a*-2*i* are also adopted from Kumana et al., supra., which is incorporated herein by reference in its entirety.

FIG. 3 shows the clinicopathologic features and outcome of 12 consecutive patients with relapsed acute promyelocytic leukemia (APL) treated with oral $As_2O_3$. FIG. 3 is adopted from Au et al., *Blood* (2003) 102:407-8, which is incorporated herein by reference.

5. DETAILED DESCRIPTION OF THE INVENTION 5.1 Preparation of the Oral Arsenic Trioxide Composition In the absence of commercially available pharmacopoeial grade $As_2O_3$, a powder of good chemical quality (minimum purity 99%) was obtained from Sigma Chemical Company (St Louis, Mo., USA). $As_2O_3$ powder is sparingly and extremely slowly soluble in cold water; even in boiling water it is only soluble in a 1:15 ratio (Arsenic Trioxide, In: Budavari S O'Neil M J (Eds), The Merck Index. An encyclopedia of chemicals, drugs and biologicals. NJ: Merck & Co., Inc. 11th Ed., Rahway, N.J., USA. 1989. Monograph 832, p 127). It was eventually dissolved as follows.

Accurately weighed 500 mg aliquots of $As_2O_3$ powder were poured into a beaker containing 150 ml of sterile water. The resulting suspension was dissolved by drop-wise addition of 3M Sodium Hydroxide. When the powder was completely dissolved, a further 250 ml of sterile water were added. Using a pH meter, the ensuing solution was adjusted to pH 8.0 by slow titration with 6M Hydrochloric acid (HCl). Subsequent adjustment of the pH to 7.2 was carried out with dilute HCl and sterile water added to make up a final volume of 500 ml. Due to the extremely poisonous nature of the raw material and the known liability of such solutions to support fungal growths, the entire process was conducted in a pharmaceutical isolator. Contrary to general recommendations in Pharmacopoeias, no fungicidal agent was added. The resulting clear solution was developed to contain $As_2O_3$ at a concentration of 1 mg/ml. Moreover, samples submitted to the Hong Kong Government Laboratory were assayed and confirmed to contain 1 mg of $As_2O_3$ per ml and there was no fungal growth after incubation for 1 month in a sample submitted to the Department of Microbiology. The shelf-life of the solution was in excess of 3 months and for purpose of this study, no patient received formulations that had been stored for longer periods.

5.2 Methods of Use 5.2.1 Use in Subjects with Hematological Malignancies

The present invention further provides methods of using the oral arsenic trioxide compositions of the invention. In one embodiment, the arsenic trioxide composition is used as a medicament for treatment of hematological malignancies (e.g., leukemia, Hodgkin's disease, non-Hodgkin's lymphoma, and myeloma). The methods comprise administering an effective amount of the arsenic trioxide composition to a subject in need. The arsenic trioxide composition may be administered orally, in liquid or solid form, or enterally through a feeding tube. As used herein, the term "an effective amount" means an amount sufficient to provide a therapeutic or healthful benefit in the context of hematological malignancies.

In one embodiment, the arsenic trioxide composition can produce a healthful benefit in a subject suffering from hematological malignancies. Preferably, the subject is a human being. The subject in need is one who is diagnosed with hematological malignancies, with or without metastasis, at any stage of the disease. As used herein, the term "hematological malignancies" include but are not limited to leukemia, lymphoma, and myeloma. As used herein, the term "leukemia" includes but is not limited to acute lymphocytic leukemia (ALL); acute myeloid leukemia (AML) (sometimes called acute nonlymphocytic leukemia (ANLL)) such as myeloblastic, promyelocytic, myelomonocytic, monocytic, erythroleukemia leukemias and myelodysplastic syndrome; chronic lymphocytic leukemia (CLL); chronic myeloid (granulocytic) leukemia (CML); chronic myelomonocytic leukemias (CMML); hairy cell leukemia; and polycythemia vera. As used herein, the term "lymphoma" includes but is not limited to Hodgkin's disease and non-Hodgkin's lymphoma. As used herein, the term "myeloma" includes but is not limited to giant cell myeloma, indolent myeloma, localized myeloma, multiple myeloma, plasma cell myeloma, sclerosing myeloma, solitary myeloma, smoldering multiple myeloma, nonsecretary myeloma, osteosclerotic myeloma, plasma cell leukemia, solitary plasmacytoma, and extramedullary plasmacytoma.

The subject may be a patient who is receiving concurrently other treatment modalities against the hematological malignancies. The subject can be a patient with hematological malignancies who had undergone a regimen of treatment (e.g., chemotherapy and/or radiation) and whose cancer is regressing. The subject may be a patient with hematological malignancies who had undergone a regimen of treatment and who appears to be clinically free of the hematological malignancies. The arsenic trioxide composition of the invention can be administered adjunctively with any of the treatment modalities, such as but not limited to chemotherapy and/or radiation. For example, the arsenic trioxide composition can be used in combination with one or more chemotherapeutic or immunotherapeutic agents, such as amsacrine (AMSA), busulfan (Myleran®), chlorambucil (Leukeran®), cladribine (2-chlorodeoxyadenosine; "2-CDA"; Leustatin®), cyclophosphamide (Cytoxan®), cytarabine (ara-C;Cytosar-U®), daunorubicin (Cerubidine®), doxorubicin (Adriamycin®), etoposide (VePesid®), fludarabine phosphate (Fludara®), hydroxyurea (Hydrea®), idarubicin (Idamycin®), L-asparaginase (Elspar®), methotrexate sodium plus 6-mercaptopurine (6-MP; Purinethol®), mitoxantrone (Novantrone®), pentostatin (2-deoxycoformycin; "DCF"; Nipent®), prednisone, retinoic acid (ATRA), vincristine sulfate (Oncovin®), 6-thioguanine (Tabloid®), cyclosporin A, Taxol®), Cisplatin®, Carboplatin®, Doxil®, Topotecan®, Methotrexate®, Bleomycin®, and Epirubicin®. The arsenic trioxide composition can also be used after other regimen(s) of treatment is concluded.

The subject may be one who has not yet been diagnosed with hematological malignancies but are predisposed to or at high risk of developing hematological malignancies as a result of genetic factors and/or environmental factors.

Depending on the subject, the therapeutic and healthful benefits range from inhibiting or retarding the growth of the hematological malignancies and/or the spread of the hematological malignancies to other parts of the body (i.e., metastasis), palliating the symptoms of the cancer, improving the probability of survival of the subject with the cancer, prolonging the life expectancy of the subject, improving the quality of life of the subject, and/or reducing the probability of relapse after a successful course of treatment (e.g., chemotherapy, radiation). The symptoms associated with hematological malignancies include but are not limited to a weakened immune system, infections, fevers, decrease in red blood cells and platelets, weakness, fatigue, loss of appetite, loss of weight, swollen or tender lymph nodes, liver, or spleen, easy bleeding or bruising, tiny red spots (called petechiae) under the skin, swollen or bleeding gums, sweating (especially at night), bone or joint pain, headaches, vomiting, confusion, loss of muscle control, and seizures.

In particular, the invention provides a method for complete remission of the hematological malignancies in a subject, such as a human, comprising administering orally to the subject an arsenic trioxide composition of the invention. In other embodiments, the invention provides at least 10%, 20%, 40%, 60%, 80%, and 95% remission of the hematological malignancy. The invention also provide a method for prolonging the time of survival of a subject inflicted with hematological malignancies, preferably a human patient, comprising administering orally to the subject an arsenic trioxide composition of the invention.

The effective dose will vary with the subject treated and the route of administration. The effective dose for the subject will also vary with the condition to be treated and the severity of the condition to be treated. The dose, and perhaps the dose frequency, will also vary according to the age, body weight, and response of the individual subject. In general, the total daily dose range of the arsenic trioxide composition for a subject inflicted with hematological malignancies is about 1 mg, 2 mg, 3 mg, 4 mg, 5 mg, 6 mg, 7 mg, 8 mg, 9 mg, 10 mg, 15 mg, 20 mg, or 25 mg per day; preferably, about 10 mg per day, administered in single or divided doses. Preferably, the arsenic trioxide composition is administered to the subject orally.

The length of time for a course of treatment should be at least 1 day, at least 2 days, at least 3 days, at least 4 days, at least 5 days, at least 6 days, at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, or at least 1 year. It may be necessary to use dosages outside these ranges in some cases as will be apparent to those skilled in the art. In certain embodiments, the arsenic trioxide compositions can be administered for a period of time until the symptoms are under control, or when the disease has regressed partially or completely. Further, it is noted that the clinician or treating physician will know how and when to interrupt, adjust, or terminate use of the arsenic trioxide composition as a medication in conjunction with individual patient response.

The effect of the arsenic trioxide compositions of the invention on development and progression of hematological malignancies can be monitored by any methods known to one skilled in the art, including but not limited to measuring: a) changes in the size and morphology of the tumor using imaging techniques such as a computed tomographic (CT) scan or a sonogram; and b) changes in levels of biological markers of risk for hematological malignancies.

In certain embodiments, toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

In other embodiments, the data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the scid mouse model or transgenic mice. The following are some assays provided as examples and not by limitation.

5.2.2 Formulation

The compositions of the present invention comprise arsenic trioxide prepared as described above in Section 5.1, as active ingredient, and can optionally contain a pharmaceutically acceptable carrier or excipient, and/or other ingredients provided that these ingredients do not compromise (e.g., reduce) the efficacy of the arsenic trioxide compositions. Other ingredients that can be incorporated into the arsenic trioxide compositions of the present invention, may include, but are not limited to, herbs (including traditional Chinese medicine products), herbal extracts, vitamins, amino acids, metal salts, metal chelates, coloring agents, flavor enhancers, preservatives, and the like.

Any dosage form may be employed for providing the subject with an effective dosage of the oral composition. Dosage forms include tablets, capsules, dispersions, suspensions, solutions, and the like. In one embodiment, compositions of the present invention suitable for oral administration may be presented as discrete units such as capsules, blisters, cachets, or tablets, each containing a predetermined amount of activated and conditioned yeast cells, as a powder or granules or as a solution or a suspension in an aqueous liquid, a non-aqueous liquid, an oil-in-water emulsion, or a water-in-oil liquid emulsion. In preferred embodiments, the oral composition is in the form of a solution. In general, the compositions are prepared by uniformly and intimately admixing the active ingredient with liquid carriers or finely divided solid carriers or both, and then, if necessary, shaping the product into the desired presentation. Such products can be used as pharmaceuticals or dietary supplements, depending on the dosage and circumstances of its use.

The oral compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Liquid preparations for oral administration can take the form of, for example, solutions, syrups or suspensions, or they can be presented as a dry product for constitution with water or other suitable vehicle before use. The temperature of the liquid used to reconstitute the dried product should be less than 65° C. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). As described below, the preparations can also be made to resemble foods or beverages, containing buffer salts, flavoring, coloring and sweetening agents as appropriate.

In certain embodiments, the arsenic trioxide composition is a suspension comprising about 0.1, 0.2, 0.3, 0.4, 0.5, 1, 2, 3, 4, 5, 10 or 15 mg of arsenic trioxide per ml. The arsenic trioxide composition can be diluted or concentrated using methods well known to those skilled in the art. In less preferred embodiments, the arsenic trioxide composition is a suspension containing about 0.1 to 100 mg arsenic trioxide per ml. In preferred embodiments, the arsenic trioxide composition is a suspension containing about 0.5 to 10 mg arsenic trioxide per ml. In more preferred embodiments, the arsenic trioxide composition is a suspension containing about 1 mg arsenic trioxide per ml. In most preferred embodiments, the arsenic trioxide composition is a suspension containing 1 mg arsenic trioxide per ml. The arsenic trioxide composition can be formulated as a health drink and packaged in liquid containers, each containing a predetermined amount of the liquid yeast culture. Standard methods of quality control and packaging are applied to produce in one embodiment of the invention, arsenic trioxide compositions packaged in liquid containers each comprising about 1 ml, 2 ml, 3 ml, 4 ml, 5 ml, 10 ml, 15 ml, 20 ml, 30 ml, 40 ml, 50 ml, 75 ml, 100 ml, 150 ml, 200 ml, 250 ml, 500 ml, 750 ml, or 1,000 ml of the arsenic trioxide composition. The number of container to be taken each day to obtain the total daily dose in a subject depends on the concentration of the arsenic trioxide compositions contained within each container.

Generally, because of their ease of administration, tablets and capsules represent the most advantageous oral dosage unit form, in which case solid pharmaceutical carriers as described above are employed. In a preferred embodiment, the composition is a capsule. The capsules can be formulated by any commercially available methods. In certain embodiments, the composition is a capsule containing 0.25 mg, 0.5 mg, 1 mg, 5 mg, 10 mg, 15 mg, 20 mg, 25 mg, 30 mg, 40 mg, or 50 mg of the arsenic trioxide compositions in powder form.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2); interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat;

imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

The invention is further defined by reference to the following example describing in detail the clinical trials conducted to study the efficacy and safety of the arsenic trioxide compositions of the invention.

6. EXAMPLES

The following examples illustrate the oral formulation of arsenic trioxide of the present invention and the results of the clinical study using the formulation. These examples should not be construed as limiting.

6.1 Example 1

The clinical study was conducted to test whether the systemic bioavailability of the oral formulation of the present invention is comparable to intravenous administration and to delineate the extent of $As_2O_3$ accumulation in the cellular components of blood and, by inference, the extent of $As_2O_3$ accumulation in bone marrow cells which are the presumed sites of action.

6.1.1 Preparation of Oral Arsenic Trioxide ($As_2O_3$) Formulation

The oral formulation of arsenic trioxide was prepared according to the method described in Section 5.1, supra. Contrary to general recommendations in Pharmacopoeias, no fungicidal agent was added. The resulting clear solution was developed to contain $As_2O_3$ at a concentration of 1 mg/ml. Moreover, samples submitted to the Hong Kong Government Laboratory were assayed by Indicative Coupled Plasma (ICP) and volumetric titration and confirmed to contain 1 mg of $As_2O_3$ per ml (see Table 1). Furthermore, there was no fungal growth after incubation for 1 month in a sample submitted to the Department of Microbiology. The shelf-life of the solution was in excess of 3 months and for purpose of this study, no patient received formulations that had been stored for longer periods.

TABLE 1

| SAMPLES (Analysis date) | ARSENIC (Expressed as arsenic trioxide) |
| --- | --- |
| A (Aug. 16, 2000-Aug. 18, 2000) | 1.00 mg/ml |
| B (Jan. 21, 2002-Feb. 2, 2002) | 1.00 mg/ml |
| C (Jan. 21, 2002-Feb. 2, 2002) | 1.06 mg/ml |

6.1.2 Patients

Written informed consent to participate in the study was obtained from nine (9) patients with relapsed acute myeloid leukemia (AML) or relapsed acute promyelocytic leukemia (APL), all of whom had failed to respond to at least two standard anti-leukemic regimens. Demographic features as well as details pertaining to each patient's disease state (including laboratory findings) were recorded throughout the period of study. Their subsequent clinical progress and pertinent laboratory results were also logged. The University of Hong Kong Faculty of Medicine Ethics Committee approved the entire protocol.

6.1.3 Treatment Protocol and Blood Sampling

As diets containing seafood contain arsenic, each patient was instructed to refrain from seafood, preferably for at least one week before arsenic administration. On day-1 at 10 A.M., 10 mg of a standard, commercially available IV $As_2O_3$ formulation (from Ophthalmic Laboratories, Sydney, Australia) diluted in 100 ml of Sodium Chloride 0.9% solution was infused IV over 60 minutes. At 10 A.M. on day-2 (i.e., 24 hours after the start of the IV infusion), each patient swallowed a 10 mg dose (10 ml) of our oral $AS_2O_3$ solution and none were instructed to fast before or during their treatment.

Venous blood samples were drawn (11 ml) prior to $As_2O_3$ administration on day-1 and subsequently at the following times after the beginning of the IV infusion: 1, 2, 3, 4, 6, 8, 24, 25, 26, 27, 28, 30, 32 and 48 hours. Five ml from each sample were collected in a non-gel lithium-heparin tube (for determination of plasma arsenic level) and 3 ml×2 in EDTA tubes (for determination of whole blood level). The plasma from the lithium-heparin tube was freshly separated and both the plasma and whole blood samples were stored at 4° C. and subsequently analyzed in batches.

6.1.4 Assay of Arsenic Concentration

Plasma and whole blood arsenic concentration were assayed after the samples were deproteinized with 3% (w/v) trichloroacetic acid and then mixed with matrix modifiers. The matrix modifiers contained magnesium nitrate (10 g/L), palladium chloride (6 g/L), and ammonium sulphite (20 g/L) in 0.5% Triton X 100. All chemicals were of analytical grade and were obtained from Sigma (St Louis, Mo.). The treated samples were assayed for total arsenic concentration in whole blood and plasma (which includes $As_2O_3$ per se and its metabolites) by graphite furnace atomic absorption spectrophotometry (Simma 6000, Perkin-Elmer, Norwalk, Conn.). Concentrations are therefore expressed as nmol/L of arsenic above basal values. The between-day coefficient of variation of this method was 7.5-9.6% for arsenic concentrations varying from 559 to 2169 nmol/L. The accuracy of this method was assessed by spiking known amounts of arsenic into patient samples; recovery being 97.3-101.3% for concentrations varying from 301 to 678 nmol/L.

6.1.5 Oral Arsenic Bioavailability Determination

For each patient, plasma and whole blood concentration versus time plots following intravenous and oral $As_2O_3$ were compared. Using standard computer software (GraphPad Prism® Version 3) incorporating the trapezoid rule, the area under each arsenic level versus time curve (AUC) was derived for the periods 0 to 24 hours after starting IV dosing (taken to be 100%) and 0 to 24 hours after oral dosing (i.e., 24 to 48 hours after IV dosing) and used as measures of bioavailability.

To derive the 24-48 hour arsenic level versus time curve (AUC) attributable to the intravenous infusion, it was assumed that the elimination of arsenic eventually approximates to mono-exponential decay. On that basis, log arsenic concentration versus time plots of individual patients (covering periods up to 24 hours post intravenous dosing) were submitted to regression analysis, using customized computer software developed by The University of Hong Kong Computer Centre. The highest ensuing regression value ($r^2$) associated with a negative slope (indicating decaying concentration) was selected for subsequent calculations; all such computations being based on a minimum of 3 points. For example, if after intravenous dosing $r^2$ values for data sets from 1-24, 2-24, 3-24, 4-24 and 6-24 hours were 0.53, 0.62, 0.80, 0.95, and 0.94L respectively, then the data set from 4-24 hours would be used for the calculation, provided its slope was negative. From the selected data set, the following parameters were then generated: β-elimination phase first order elimination rate constant (Ke), elimination half-life (T½), and extrapolated zero time concentration (C0). For each patient, these parameters were used to estimate an extrapolated 24-48 hour AUC attributed to intravenous dosing. The difference between the latter AUC and the actual (or gross) 24 to 48 hour AUC (see FIG. 1) was regarded as the net 0 to 24 hour AUC attributable to oral dosing.

6.1.6 Estimating Arsenic in the Cellular Fraction of Blood

The concentration of arsenic in the cellular fraction of blood (Cc) at 48 hours after the initial intravenous dose was calculated from the corresponding plasma (Cp) and whole blood (Cb) concentrations and the prevailing hematocrit (Hct) value as follows:

Nano mols of arsenic in the plasma from 1 liter of blood=Cp(1-Hct).

Accordingly, the mass of arsenic in the remaining cellular fraction in 1 liter of blood amounts to Cb-[Cp(1-Hct)].

Thus, the concentration (weight/volume) of arsenic per liter of the cellular fraction of the blood Cc={Cb-[Cp(1-Hct)]}/Hct.

6.1.7 Results

The demographic features, basal arsenic concentrations, disease status, and treatment outcomes of each patient are shown in Table 2. In our laboratory, accepted normal ranges are as follows: Urea 3.2-7.5 mM/L; Creatinine 86-126 μM/L; alanine transaminase (ALT) 5-63 U/L and aspartate transaminase (AST) 13-33 U/L. Regularly performed ECGs on all the patients receiving $As_2O_3$, yielded no instance of abnormal QTc prolongation.

TABLE 2

| | Sex/Age | Ht (cm)/Wt (Kg) | Urea (mM/L)/Creatinine (μM/L) † | ALT/AST (U/L) † | Basal Arsenic concentration | | Diagnosis & response to oral $As_2O_3$ |
|---|---|---|---|---|---|---|---|
| | | | | | Plasma (nM/L) | Blood (nM/L) | |
| 1 | M/29 | 163/45.5 | 3.0/57 | 7/6 | 74 | 150 | Refractory AML, no response |
| 2 | M/67 | 162/54 | 4.0/84 | 72/44 | 232 | 193 | Refractory AML, no response |
| 3 | M/69 | 162/52.8 | 8.6/89 | 50/55 | 33 | 108 | Refractory AML, no response |
| 4 | F/31 | 158/53 | 3.4/50 | 63/30 | 33 | 46 | Refractory AML, no response |
| 5 | F/17 | 158/45.1 | 3.2/49 | 5/23 | 33 | 33 | Relapsed APL, complete |
| 6 | M/33 | 174/69.7 | 3.2/77 | 35/38 | 33 | 33 | Relapsed APL, complete |
| 7 | M/34 | 154/70 | 3.9/101 | 11/12 | 68 | 66 | Relapsed APL, complete |

TABLE 2-continued

| Sex/ Age | Ht (cm)/ Wt (Kg) | Urea (mM/L)/ Creatinine (μM/L) † | ALT/ AST (U/L) † | Basal Arsenic concentration | | Diagnosis & response to oral As$_2$O$_3$ |
|---|---|---|---|---|---|---|
| | | | | Plasma (nM/L) | Blood (nM/L) | |
| 8 M/33 | 166/63 | 3.9/93 | 37/35 | 33 | 33 | Relapsed APL, complete |
| 9 F/47 | 163/73 | 5.0/74 | 28/18 | 46 | 125 | Relapsed APL, complete |

The day-2 mean plasma and blood arsenic level versus time curve (AUC) attributed to oral dosing were 99% and 87%, respectively, of corresponding day-1 values. On average, 48-hour blood cell arsenic levels were 270% greater than in plasma (p=0.013). No patient suffered unexpected complications.

Four (4) patients had relapsed/refractory acute myeloid leukemia (AML), and five (5) had relapsed and acute promyelocytic leukemia (APL). None with refractory AML responded hematologically and all died subsequently from leukemia. All five (5) with relapsed APL achieved a complete hematological remission and were alive as of April, 2002; the median duration of survival since starting arsenic therapy being 11 months and since diagnosis 36 months (ranging 20-56 months). For three (3) patients (7, 8 and 9) with relapsed APL, rapid progression of their leukemia necessitated treatment before they refraining from seafood for an entire week. FIGS.2a-2i illustrate the plasma and blood arsenic concentration versus time plots of the nine (9) patients studied. Concerning systemic bioavailability of our oral formulation of As$_2$O$_3$, Table 3 summarizes the AUC findings with respect to IV and oral dosing. Table 4 lists the prevailing hemoglobin and hematocrit values of these patients at the time they were studied and the plasma and estimated cellular arsenic concentrations at 48-hours. On average, cellular As concentrations exceeded plasma concentration by 270%.

TABLE 4

| Pt No. | Hgb g/dL | HCT (L) | Plasma Conc nM/L (Cp) | Cellular Conc nM/L (Cc) | Difference nM/L |
|---|---|---|---|---|---|
| 1 | 7.9 | 0.23 | 102 | 50 | −52 |
| 2 | 7.6 | 0.21 | 38 | 52 | 14 |
| 3 | 8.3 | 0.24 | 68 | 595 | 527 |
| 4 | 9.2 | 0.27 | 55 | 243 | 188 |
| 5 | 8.7 | 0.25 | 152 | 591 | 439 |
| 6 | 15.6 | 0.44 | 49 | 227 | 178 |
| 7 | 12.3 | 0.35 | 180 | 299 | 119 |
| 8 | 15.8 | 0.46 | 32 | 133 | 101 |
| 9 | 10.5 | 0.31 | 88 | 384 | 295 |
| Mean (± SE) | 10.7 (1) | 0.31 (0.03) | 85 (17) | 286 (68) | 201* (63) |

*p = 0.013; two tailed paired t-test.

6.1.8 Discussion 6.1.8.1 Bioavailability

A randomized balance sequence of dosing was not used in this study, as we wanted to know how each patient tolerated As$_2$O$_3$ at the outset, when 100% systemic availability was assured (after IV dosing). Based on the AUCs under respective time versus plasma and whole blood concentration plots (FIG. 1 and Table 3), it was evident that our oral formulation achieved acceptable bioavailability in comparison to IV dos-

TABLE 3

AUC of arsenic Concentrations (nanomolar-hours)

| | | Day 1: 0-24 h after starting IV dose | | Day2: 24-48 h after starting IV dose | | |
|---|---|---|---|---|---|---|
| | Patient | AUC | Estimated β slope Regression (No. of Points) | Gross AUC 0-24 h post oral dose | Extrapolated AUC due to IV dose on day 1 | Attributed Net AUC 0-24 h post oral dose (% of day 1 AUC) |
| 1 | Plasma | 2923 | 0.95 (4) | 4317 | 1466 | 2851 (98) |
| | Blood | 2852 | 0.23 (7) | 3794 | 1512 | 2282 (80) |
| 2 | Plasma | 3367 | 0.99 (6) | 2661 | 20 | 2641 (78) |
| | Blood | 2261 | 0.43 (6) | 1558 | 926 | 632 (28) |
| 3 | Plasma | 2828 | 0.02 (7) | 3146 | 1605 | 1541 (54) |
| | Blood | 3120 | 0.09 (4) | 5019 | 2800 | 2219 (71) |
| 4 | Plasma | 881 | 0.56 (7) | 2192 | 0 | 2192 (249) |
| | Blood | 2971 | 0.62 (3) | 3355 | 1908 | 1447 (49) |
| 5 | Plasma | 4091 | 0.87 (7) | 5411 | 1294 | 4117 (101) |
| | Blood | 6235 | 0.99 (3) | 8825 | 2636 | 6189 (99) |
| 6 | Plasma | 2173 | 0.41 (7) | 2917 | 1181 | 1736 (80) |
| | Blood | 2785 | 0.99 (3) | 5565 | 402 | 5164 (185) |
| 7 | Plasma | 4047 | 0.45 (6) | 5899 | 1685 | 4214 (104) |
| | Blood | 5903 | 0.83 (3) | 6713 | 4323 | 2390 (40) |
| 8 | Plasma | 1553 | 0.73 (5) | 1641 | 180 | 1461 (94) |
| | Blood | 2877 | 0.98 (3) | 3808 | 130 | 3679 (128) |
| 9 | Plasma | 2193 | 0.99 (3) | 4079 | 1075 | 3004 (137) |
| | Blood | 4311 | 1.00 (3) | 6594 | 1730 | 4864 (113) |
| Mean ± SE | | 2673 ± 362 | 0.67 ± 0.11 (5.8 ± 0.5) | 3585 ± 481 | 945 ± 229 | 2640 ± 343 (111 ± 19) |
| Plasma 95% CI | | 1839-3507 | 0.40-0.91 (4.6-6.9) | 2475-4695 | 417-1474 | 1850-3430 (67-154) |
| Mean ± SE | | 3702 ± 483 | 0.68 ± 0.12 (3.9 ± 0.5) | 5026 ± 725 | 1819 ± 436 | 3207 ± 623 (88 ± 16) |
| Blood 95% CI | | 2587-4816 | 0.41-0.96 (2.7-5.1) | 3354-6698 | 814-2823 | 1771-4643 (50-126) | ing. Although there was considerable inter-patient variation, intra-patient (inter-day) variation was relatively small. Whereas the AUCs after oral $As_2O_3$ appeared to be nearly the same as those after IV dosing certain anomalies require explanation. Thus, for patients 6, 8 and 9—whole blood AUCs attributable to oral dosing were markedly greater than after IV dosing and the same was true for plasma AUCs of patients 4 and 9. Possible reasons include: i) problems with arsenic dosing or drug level measurements; ii) after the first (IV) dose, $As_2O_3$ saturates tissue binding sites such that more is available in the blood following the second (oral) dose; and iii) day-2 dietary indiscretions by individual patients.

Although it is uncertain whether they were due to differing disease states, differences in patient physiology, or other factors, there were considerable inter-individual variations in plasma and whole blood AUCs among the nine (9) patients (Table 3); up to approximately 5 and 10 fold, respectively. The possible importance of such inter-individual variations in dosage/drug level relationships to the efficacy and toxicity of $As_2O_3$ needs further exploration.

6.1.8.2 Concentration in Cells

It is well recognized that $As_2O_3$ is concentrated in certain tissues of the body (Yamauchi H. et al., 1985, Metabolism and excretion of orally administered arsenic trioxide, *Toxicology* 34:113-21; Huang SY et al., 1998, Acute and chronic arsenic poisoning associated with treatment of acute promyelocytic leukemia, *Brit. J Haemat.* 103:1092-5; Ni J H et al., 1998, Pharmacokinetics of intravenous arsenic trioxide in the treatment of acute promyelocytic leukemia, *Chinese Medical J.* 111:1107-10). Our findings support this observation in that 48-hour concentrations in the cellular fraction of the blood were consistently higher (by about 2 to 3 fold) than corresponding plasma concentrations, except in patient no 1. The latter was very ill and anemic (Table 4) and, on day-1 of the $As_2O_3$ therapy, received 2 units of packed cells, which possibly diluted levels of whole blood arsenic. As an aid to monitoring $As_2O_3$ therapy, arsenic concentrations achieved in the cellular fraction of blood (which presumably parallel those in cellular elements of bone marrow) may turn out to be critical for achieving a given response and/or avoiding toxicity.

This study clearly showed that the oral formulation of the present invention achieves comparable arsenic bioavailability to IV dosing. Moreover, five (5) of our patients (all with relapsed APL) who have continued to receive repeated courses of our oral formulation have faired remarkably well. Thus, the use of the oral $As_2O_3$ formulation of the present invention is an important advance which offers improved convenience and cost-effectiveness for patients. The results of our study also showed that arsenic is concentrated in the cellular elements of blood. Thus, monitoring arsenic in blood, especially its cellular fraction, is very likely a useful means for improving efficacy and safety of the treatment, allowing more customized $As_2O_3$ therapy to patients.

6.1.8.3 Conclusions

The oral $As_2O_3$ formulation of the present invention was more convenient and cost-effective than IV administration of the compound. Furthermore, the systemic bioavailability of arsenic was comparable to that of IV administration and arsenic was concentrated in the cellular fraction of blood 48 hours after starting $As_2O_3$ treatment.

6.2 Example 2

The following examples illustrate the healthful benefits of using the oral formulation of arsenic trioxide of the present invention and the results of the clinical study using the formulation. These examples should not be construed as limiting.

6.2.1 Preparation of Oral Arsenic Trioxide ($As_2O_3$) Formulation

The oral arsenic trioxide formulation (oral-$As_2O_3$) was prepared in a similar manner as described in Section 6.1.1.

6.2.2 Patients

Twelve consecutive unselected patients with relapsed APL were treated with oral-$As_2O_3$ (see Table 4). The relapse was confirmed morphologically (>30% blasts+abnormal promyelocytes in the marrow) and cytogenetically (presence of t(15;17), with none of the cases showing additional karyotyic aberrations) or molecularly (presence of PML/RARA). The treatment was given with informed consent, and the protocol was approved by the University of Hong Kong Faculty of Medicine Ethics Committee.

All patients had a pre-treatment Karnofsky score of >80%. Routine monitoring included alternate-daily blood counts and renal/liver function tests, and electrocardiography daily in the initial week, then weekly.

6.2.3 Treatment Protocol

Eight patients in first relapse (R1) were treated with oral-$As_2O_3$ (10 mg/day) until complete remission (CR, <5% of abnormal promyelocytes+blasts in the marrow), followed by consolidation with idarubicin (6 mg/m²/day, 5 days in the first month, then two days per month for two months) (Kwong Y. L. et al. Arsenic trioxide- and idarubicin-induced remissions in relapsed acute promyelocytic leukaemia: clinicopathological and molecular features of a pilot study. *Am J Hematol.* 2001;66:274-9). Patient no. 1, 2, 3, 5 and 7 received one day of intravenous-$As_2O_3$ as part of the initial pharmacokinetic study (Kumana C. R. et al. Systemic availability of oral arsenic-trioxide used for treatment of patients with haematological malignancies. *Eur J Clin Pharmacol.* 2002;58:521-526).

Five patients in second relapse (R2) (including case 1 who relapsed after CR2) were treated with a combination of oral-$As_2O_3$ (10 mg/day) and all-trans retinoic acid (ATRA) (45 mg/m²/day) until remission (Au W. Y. et al. Combined arsenic trioxide and all-trans retinoic acid treatment for acute promyelocytic leukaemia recurring from previous relapses successfully treated using arsenic trioxide. *Br J Haematol.* 2002;117: 130-2), followed by six consolidation courses with $As_2O_3$ and ATRA ($As_2O_3$: 10 mg/day, ATRA: 45 mg/m²/day, for two weeks every two months).

6.2.4 Results

All patients in first relapse (RI) treated with oral-$As_2O_3$ (10 mg/day) for a median of 37 (22-59) days achieved second complete remission (CR2). At a median follow up of 14 (6-18) months, seven patients were in continuous CR2.

Four patients in second relapse (R2) treated with oral-$As_2O_3$/ATRA for a median of 31 (28-37) days achieved third complete remission (CR3). At a median follow-up of 17 (14-19) months, all had remained in CR3. Patient no. 1 died of cerebral hemorrhage 76 days post-treatment, without achieving CR3.

The level of promyelocytic leukemia-retinoic acid receptor alpha (PML/RARA) remained positive in all patients after $As_2O_3$-induced CR. However, PML/RARA became negative in 11 cases 3-6 months post-remission, and remained negative until the latest bone marrow examination. PCR in patient no. 1 became positive shortly before R2.

Four patients (patient no. 1, 4, 10 and 12) developed leucocytosis (median 74 (62-120)×10⁹/L) requiring idarubicin (6 mg/m²/day×5, given when white cell count>15×10⁹/L) for control. However, symptomatology similar to the ATRA syndrome (Camacho L. H. et al. Leukocytosis and the retinoic acid syndrome in patients with acute promyelocytic leukemia treated with arsenic trioxide. *J Clin Oncol.* 2000;18:2620-5) was not observed.

Impairment of liver function tests (LFT) occurred in five patients, peaking at a median of 11 (5-21) days. LFT normalized after temporary cessation of treatment, and further oral-$As_2O_3$ therapy was not compromised. Mild skin rashes (grade I) developed in five patients and subsided with symptomatic treatment. Headache developed in two patients on oral-$As_2O_3$/ATRA, and subsided with splitting the dose of ATRA. None of our patients showed ECG abnormalities of the types previously reported (Ohnishi K. et al. Prolongation of the QT interval and ventricular tachycardia in patients treated with arsenic trioxide for acute promyelocytic leukemia. *Ann Intern Med.* 2000;133:881-5).

6.2.5 Discussion

Our preliminary results in this pilot study showed that oral-$As_2O_3$ was highly active in relapsed APL, with an efficacy comparable to intravenous-$As_2O_3$ (Tallman M. S. et al. Acute promyelocytic leukemia: evolving therapeutic strategies. *Blood* 2002;99:759-67). The side effects, including the frequency and severity of leukocytosis, LFT derangement and skin rashes, were also comparable with intravenous-$As_2O_3$ (Niu C. et al. Studies on treatment of acute promyelocytic leukemia with arsenic trioxide: remission induction, follow-up, and molecular monitoring in 11 newly diagnosed and 47 relapsed acute promyelocytic leukemia patients. *Blood* 1999; 94:3315-24; Soignet S. L. et al. United States multicenter study of arsenic trioxide in relapsed acute promyelocytic leukemia. *J Clin Oncol.* 2001;19:3852-60). Cardiac arrhythmias were not found, which was similar to a previous study of intravenous-$As_2O_3$ in Chinese patients, where arrhythmia was seen in only 1/58 patients (Niu C. et al., supra.).

It is important to note that only four patients received oral-$As_2O_3$ as a single agent for CR induction, with the rest having received ATRA or idarubicin before CR was reached. With this limitation, our results showed that oral-$As_2O_3$ had a short-term efficacy and safety profile similar to intravenous-$As_2O_3$. A recent study also showed that oral tetra-arsenic tetra-sulphide was highly efficacious in APL (Lu D. P. et al. Tetra-arsenic tetra-sulfide for the treatment of acute promyelocytic leukemia: a pilot report. *Blood* 2002;99:3136-43). However, the long-term efficacy and safety of oral-$As_2O_3$ as compared with intravenous-$As_2O_3$ will require longer follow-up.

Finally, although oral- or intravenous-$As_2O_3$ and hematopoietic stem cell transplantation are effective treatment modalities for patients with relapsed APL, their relative merits are undefined, and further randomized trials will be needed to address this issue.

7. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed:

1. A method of treating hematological malignancies in a subject in need thereof, the method comprising orally administering to the subject a therapeutically effective amount of at least 90% pure arsenic trioxide to produce a lower peak plasma concentration with less prolongation of the QT interval and ventricular tachycardia than observed when the same amount of arsenic trioxide is administered intravenously.

2. The method of claim 1, wherein the arsenic trioxide is a powder.

3. The method of claim 2, wherein the arsenic trioxide powder has at least 97%, 98% or 99% purity.

4. The method of claim 1, wherein the arsenic trioxide is incompletely dissolved or dispersed in a solution.

5. The method of claim 1, wherein the arsenic trioxide is administered in a dosage of 5 to 10 mg/day.

6. The method of claim 1, wherein the arsenic trioxide is in a solution having a pH of 8.0.

7. The method of claim 1, wherein the arsenic trioxide is in a solution having a pH of 7.2.

8. The method of claim 1, wherein the arsenic trioxide is orally administered to the subject daily at intervals for periods of weeks, a month or longer.

9. The method of claim 1, wherein the therapeutically effective amount is 10 mg per day.

10. The method of claim 1, wherein the hematological malignancies is selected from the group consisting of acute myeloid leukemia, acute nonlymphocytic leukemia, myeloblastic leukemia, promyelocytic leukemia, myelomonocytic leukemia, monocytic leukemia, erythroleukemia, myelodysplastic syndrome, acute promyclocytic leukemia, chronic lymphocytic leukemia, chronic myeloid leukemia, hairy cell leukemia, polycythemia vera, Hodgkin's lymphoma, non-Hodgkin's lymphomas, myeloma, giant cell myeloma, indolent myeloma, localized myeloma, multiple myeloma, plasma cell myeloma, sclerosing myeloma, solitary myeloma, smoldering multiple myeloma, nonsecretary myeloma, osteosclerotic myeloma, plasma cell leukemia, solitary plasmacytoma, and extramedullary plasmacytoma.

11. The method of claim 1, wherein the hematological malignancies is acute myeloid leukemia.

12. The method of claim 1, wherein the hematological malignancies is acute promyclocytic leukemia.

13. The method of claim 1 further comprising administering one or more additional chemotherapeutic agents.

14. The method of claim 1 wherein the arsenic trioxide is a in a tablet, capsule, dispersion or suspension.

* * * * *

UNITED STATES PATENT AND TRADEMARK OFFICE
CERTIFICATE OF CORRECTION

PATENT NO. : 7,521,071 B2  
APPLICATION NO. : 10/669869  
DATED : April 21, 2009  
INVENTOR(S) : Cyrus Rustam Kumana and Yok-Lam Kwong Page 1 of 1

It is certified that error appears in the above-identified patent and that said Letters Patent is hereby corrected as shown below:

Column 2, line 37, insert --2.1.4-- before "Myelodysplastic syndromes".  
Column 2, line 47, replace "causes" with --cause--.  
Column 3, line 27, replace "modem" with --modern--.  
Column 6, line 28, replace "is" with --is/are--.  
Column 6, line 58, replace "provide" with --provides--.  
Column 7, line 45, replace "uninfected" with --unaffected--.  
Column 20, line 40, replace "promyclocytic" with --promyelocytic--.  
Column 20, line 52, replace "promyclocytic" with --promyelocytic--.  
Column 20, line 55, replace "is a" with --is--.

Signed and Sealed this

First Day of September, 2009

David J. Kappos  
*Director of the United States Patent and Trademark Office*